US009228189B2

(12) United States Patent
Gryaznov et al.

(10) Patent No.: US 9,228,189 B2
(45) Date of Patent: Jan. 5, 2016

(54) C-MYC ANTISENSE OLIGONUCLEOTIDES AND METHODS FOR USING THE SAME TO TREAT CELL-PROLIFERATIVE DISORDERS

(71) Applicant: GERON CORPORATION, Menlo Park, CA (US)

(72) Inventors: Sergei M. Gryaznov, San Mateo, CA (US); Daria Zielinska, Emerald Hills, CA (US); Ronald A. Pruzan, Palo Alto, CA (US); Jeffrey N. Lindquist, Redwood City, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 13/829,594

(22) Filed: Mar. 14, 2013

(65) Prior Publication Data

US 2014/0121261 A1    May 1, 2014

Related U.S. Application Data

(60) Provisional application No. 61/719,348, filed on Oct. 26, 2012.

(51) Int. Cl.
*C07H 21/04* (2006.01)
*C12N 15/113* (2010.01)

(52) U.S. Cl.
CPC ...... *C12N 15/1135* (2013.01); *C12N 2310/314* (2013.01); *C12N 2310/315* (2013.01); *C12N 2310/341* (2013.01); *C12N 2310/343* (2013.01); *C12N 2310/345* (2013.01); *C12N 2310/3515* (2013.01)

(58) Field of Classification Search
None
See application file for complete search history.

(56) References Cited

U.S. PATENT DOCUMENTS

| 5,476,925 | A | 12/1995 | Letsinger et al. |
|---|---|---|---|
| 5,646,260 | A | 7/1997 | Letsinger et al. |
| 5,648,480 | A | 7/1997 | Letsinger et al. |
| 5,684,143 | A | 11/1997 | Gryaznov et al. |
| 5,726,297 | A | 3/1998 | Gryaznov et al. |
| 5,824,793 | A | 10/1998 | Hirschbein et al. |
| 5,837,835 | A | 11/1998 | Gryaznov et al. |
| 5,859,233 | A | 1/1999 | Hirschbein et al. |
| 5,932,718 | A | 8/1999 | Letsinger et al. |
| 5,965,720 | A * | 10/1999 | Gryaznov et al. ............ 536/23.1 |
| 6,159,946 | A * | 12/2000 | Zalewski et al. ............ 514/44 A |
| 6,608,036 | B1 | 8/2003 | Gryaznov et al. |
| 6,784,291 | B2 * | 8/2004 | Iversen et al. ............... 536/24.5 |
| 6,835,826 | B2 | 12/2004 | Gryaznov et al. |
| 6,867,294 | B1 * | 3/2005 | Sanghvi et al. ............. 536/24.5 |
| 7,138,383 | B2 | 11/2006 | Gryaznov et al. |
| 7,494,982 | B2 | 2/2009 | Gryaznov et al. |
| 7,534,878 | B2 | 5/2009 | Liu et al. |
| 7,563,618 | B2 | 7/2009 | Gryaznov et al. |
| 7,723,316 | B2 | 5/2010 | Liu et al. |
| 7,786,092 | B2 | 8/2010 | Liu et al. |
| 7,893,243 | B2 | 2/2011 | Liu et al. |
| 7,893,244 | B2 | 2/2011 | Liu et al. |
| 8,440,635 | B2 | 5/2013 | Gryaznov et al. |
| 2003/0091994 | A1 * | 5/2003 | Jenkins et al. ..................... 435/6 |
| 2003/0212032 | A1 * | 11/2003 | Gryaznov et al. .............. 514/44 |
| 2009/0227657 | A1 | 9/2009 | Liu et al. |
| 2011/0190375 | A1 | 8/2011 | Xie |
| 2012/0329858 | A1 | 12/2012 | Gryaznov et al. |
| 2013/0065950 | A1 | 3/2013 | Gryaznov et al. |
| 2013/0253042 | A1 | 9/2013 | Gryaznov et al. |
| 2014/0349292 | A1 | 11/2014 | Gryaznov et al. |

FOREIGN PATENT DOCUMENTS

| WO | 97/31009 | 8/1997 |
|---|---|---|
| WO | 02/077184 | 10/2002 |
| WO | WO-2003/070917 A2 | 8/2003 |
| WO | WO-2003/070917 A3 | 8/2003 |
| WO | 2004/029277 | 4/2004 |
| WO | 2005/023994 | 3/2005 |
| WO | 2008/094640 | 8/2008 |

OTHER PUBLICATIONS

Manoharan et al. (Antisense & Nucleic Acid Drug Dev. 2002: 103-128).*
International Search Report mailed Feb. 3, 2014 re PCT/US2013/066960 filed Oct. 25, 2013 (Geron Corporation).
Burgess, Teresa L. et al., "The Antiproliferative Activity of c-myb and c-myc Antisense Oligonucleotides in Smooth Muscle Cells is Caused By a Nonantisense Mechanism", Proc. Natl. Acad. Sci. vol. 92, 1995, pp. 4051-4055.
Carroll, Jason S. et al., "Mechanisms of Growth Arrest by c-myc Antisense Oligonucleotides in MCF-7 Breast Cancer Cells: Implications for the Antiproliferative Effects of Antiestrogens", Cancer Res, 62, 2002, pp. 3126-3131.
Dang, Chi V. , "MYC on the Path to Cancer", Cell 149, 2012, pp. 22-35.
Devi, Gayathri R. et al., "Inhibition of Human Chorionic Gonadotropin β-Subunit Modulates the Mitogenic Effect of c-myc in Human Prostate Cancer Cells", The Prostate 53, 2002, pp. 200-210.
Dikmen, Z. et al., "Telomerase targeted oligonucleotide thio-phosphoramidates in T24-luc bladder cancer cells", J. Cell. Biochem. 104, 2008, pp. 444-452.
Gewirtz, Alan M. , "Oligonucleotide Therapeutics: A Step Forward", J. Clin. Oncol., vol. 18, 2000, pp. 1809-1811.
Giles, R.V. et al., "Selecting Optimal Oligonucleotide Composition for Maximal Antisense Effect Following Streptolysin O-mediated Delivery into Human Leukaemia Cells", Nucleic Acids Research, 1998, vol. 26, No. 7, 1998, pp. 1567-1575.
Gryaznov, S. et al., "Oligonucleotide N3'-->P5' phosphoramidates as antisense agents", Nucl. Acids Res. 24(8), 1996, pp. 1508-1514.
Gryaznov, S.M. , "Oligonucleotide N3' --->P5' Phosphoramidates and thio-phosphoramidates as Potential Therapeutic Agents", Chemistry and Biology of Artificial Nucleic Acids, Wiley-VCH, Weinheim, Mar. 2012, ISBN 9783906390673, See abstract; p. 65 par 5; p. 68 par 2-3; p. 69par 4; p. 73 pars 2-3; figures 3 & 4, pp. 61-77.

(Continued)

Primary Examiner — Kimberly Chong
(74) Attorney, Agent, or Firm — Morrison & Foerster LLP

(57) ABSTRACT

Provided herein are antisense oligonucleotides that can effectively prevent or decrease c-myc protein expression as well as decrease overall rates of cell proliferation in in vitro and mammalian in vivo models of cell proliferative disorders as well as methods for using the same.

39 Claims, 14 Drawing Sheets

(56) References Cited

OTHER PUBLICATIONS

Hudziak, Robert M. et al., "Antiproliferative Effects of Steric Blocking Phosphorodiamidate Morpholino Antisense Agents Directed Against c-myc", Antisense & Nucleic Acid Drug Development 10, 2000, pp. 163-176.

Lin, Charles Y. et al., "Transcriptional Amplification in Tumor Cells with Elevated c-Myc", Cell 151, 2012, pp. 56-67.

Littlewood, Trevor D. et al., "All Things to All People", Cell 151, 2012, pp. 11-13.

Saijo, Yasuo, "Contiguous Four-guanosine Sequence in c-myc Antisense Phosphorothioate Oligonucleotides Inhibits Cell Growth on Human Lung Cancer Cells: Possible Involvement of Cell Adhesion Inhibition", Jpn. J. Cancer Res. 88, 1997, pp. 26-33.

Skorski, T. et al., "Antileukemia effect of c-myc N3'-->P5' phosphoramidate antisense oligonucleotides in vivo", Proc. Natl. Acad. Sci. USA 94, 1997, pp. 3966-3971.

Smith, J. et al., "Antisense c-myc and immunostimulatory oligonucleotide inhibition of tumorgenesis in a murine B-cell lymphoma transplant model", J. Natl. Cancer Inst. 90(15), 1998, pp. 1146-1154.

Smith, Janet B. et al., "Preclincial Antisense DNA Therapy of Cancer in Mice", Methods in Enzymology, Vo. 314, 1999, pp. 537-580.

Stein, C.A., "The Experimental Use of Antisense Oligonucleotides: a Guide for the Perplexed", J. Clin. Invest. 108, 2001, pp. 641-644.

Yin, C.Y. et al. Transcriptional Amplification in Tumor cells With Elevated C-Myc, Cell 151, Sep. 28, 2012, pp. 56-67.

Biro, S. et al., "Inhibitory effects of antisense oligonucleotides targeting c-myc mRNA on smooth muscle cell proliferation and migration", *PNAS USA* 90:654-658 (Jan. 1993).

Biroccio, a. et al. "Telomerase as a new target for the treatment of hormone refractory prostate cancer" *Endocrine-Related Cancer*, 11:407-421 (2004).

Felsher, D.W. et al., "Reversible Tumorigenesis by MYC in hematopoietic lineages", *Molecular Cell*, 4:199-207 (Aug. 1999).

Fleser, A. et al., "Efficient Reduction of Neointimal Hyperplasia in Double Injured Rabbit Carotid Arteries by Cholesterol-Conjugated Antisense *C-myc* Oligonucleotides", *JACC*, p. 290A: abstract #781-2 (Feb. 1996).

Giurato, S. et al. "Sustained regression of tumors upon MYC inactivation requires p53 or thrombospondin-1 to reverse the angiogenic switch", *PNAS* 103(44):16266-16271 (Oct. 31, 2006).

Gryaznov, S. "Oligonucleotide N3'-P5' phosphoramidates and thiophosphoramidates as potential therapeutic agents", *Chemistry & Biodiversity*, 7:477-493 (2010).

Hawley, P. et al. "Comparison of Binding of N3'→P5' Phosphoramidate and Phosphorothioate Oligonucleotides to Cell Surface Proteins of Cultured Cells", *Antisense & Nucleic Acid Drug Development* vol. 9:61-69 (1999).

Jain, M. et al. "Sustained loss of a neoplastic phenotype by brief inactivation of *MYC*" *Science*, 297:102-4 (Jul. 5, 2002).

Nie, A. et al. "c-Myc Is a Universal Amplifier of Expressed Genes in Lymphocytes and Embryonic Stem Cells", *Cell*, 151:68-79 (Sep. 28, 2012).

Rakhra, K. et al. "CD4 T Cells Contribute to the Remodeling of the Microenvironment Required for Sustained Tumor Regression upon Oncogene Inactivation", *Cancer Cell*, 18:485-498 (Nov. 16, 2010).

Shachaf, C.M. et al. "MYC inactivation uncovers pluripotent differentiation and tumor dormancy in hepatocellular cancer" *Nature*, 431:1112-1117 (Oct. 28, 2004).

Van Riggelen, J. et al. "The interaction between Myc and Miz1 is required to antagonize TGF6-dependent autocrine signaling during lymphoma formation and maintenance", *Genes & Development*, 24:1281-1294 (2010).

Waelti, E.R. et al. "Delivery to Cancer Cells of Antisense L-*myc* Oligonucleotides Incorporated in Fusogenic, Cationic-Lipid-Reconstituted Influenza-Virus Envelopes (Cationic Virosomes)", *Int. J. Cancer*, 77:728-733 (1998).

Williams, S.A. et al. "Cationic lipids reduce time and dose of *c-myc* antisense oligonucleotides required to specifically inhibit Burkitt's lymphoma cell growth" *Leukemia*, 10:1980-1989 (1996).

Wu, C.H et al. "Cellular senescence is an importance mechanism of tumor regression upon c-Myc inactivation", *PNAS*, 104(32):13028-13033 (Aug. 7, 2007).

\* cited by examiner

Figure 3:
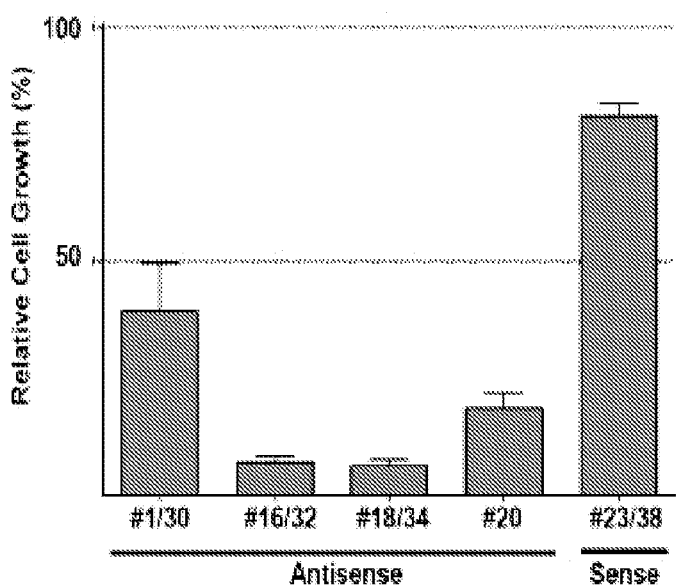
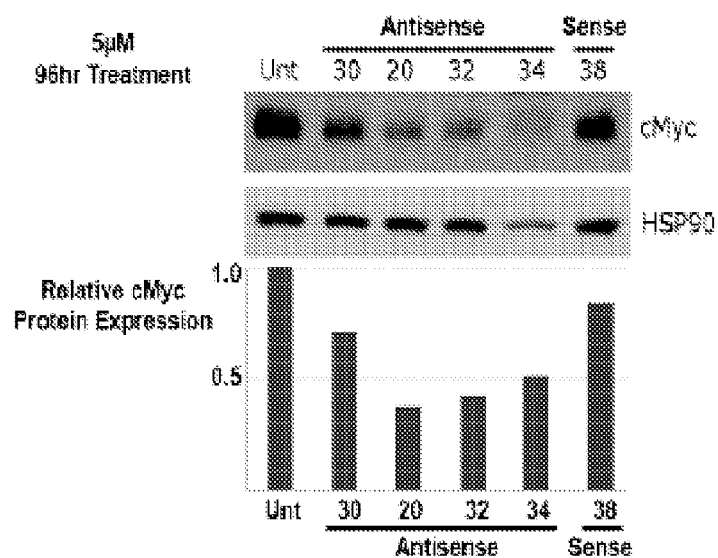

Figure 4:
A.
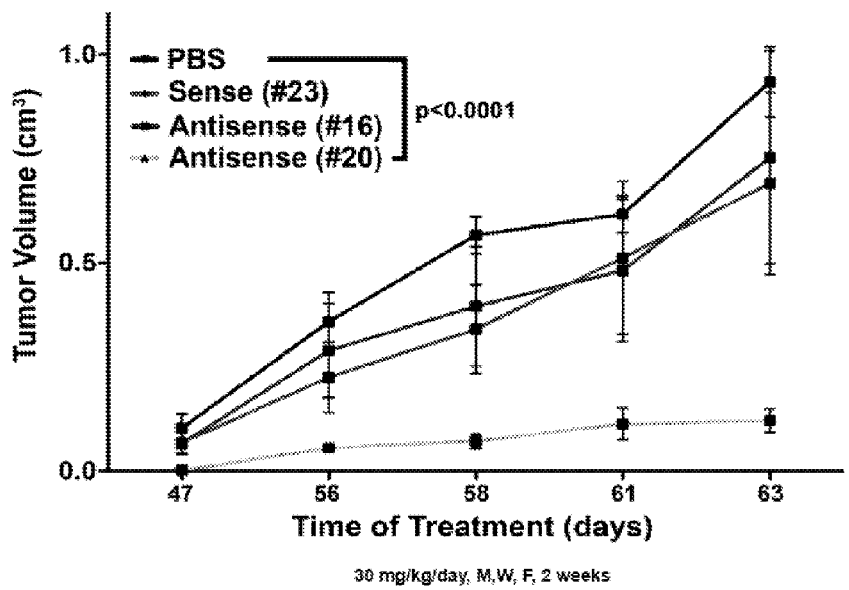
B.
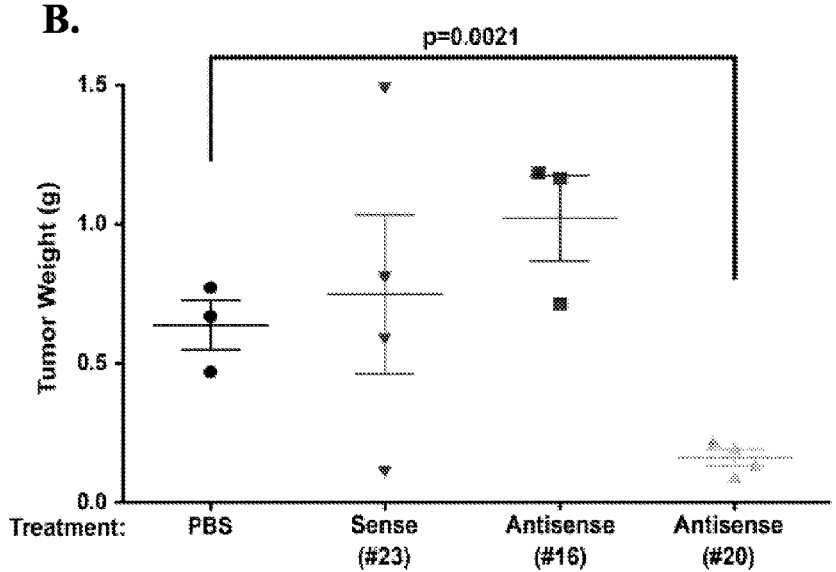

Figure 5:
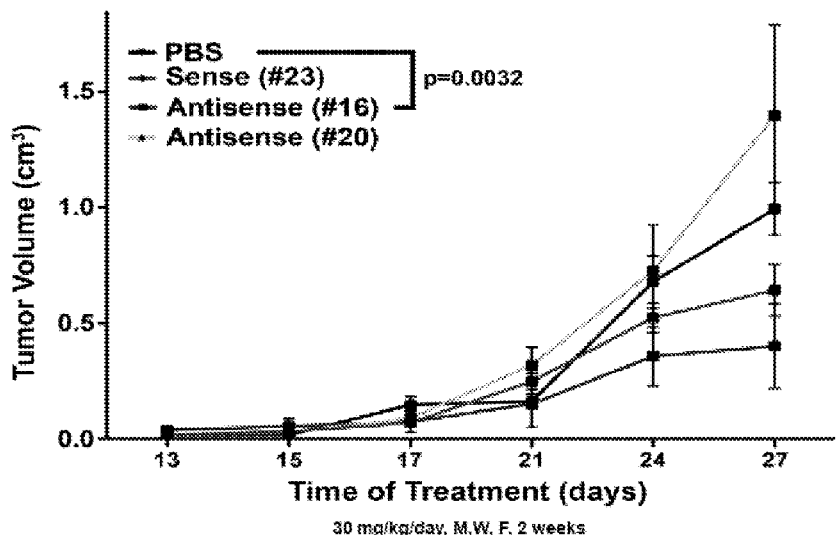
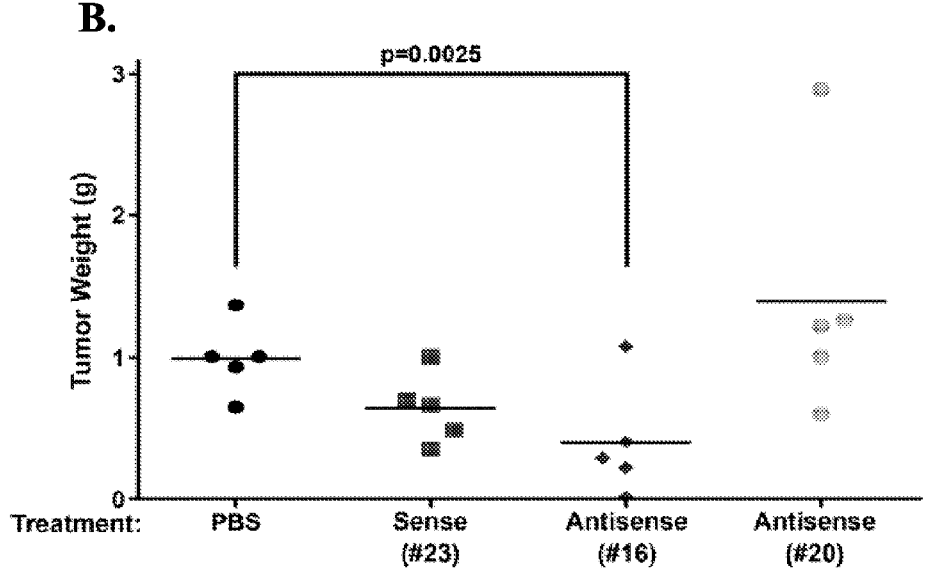

Figure 13:
A.
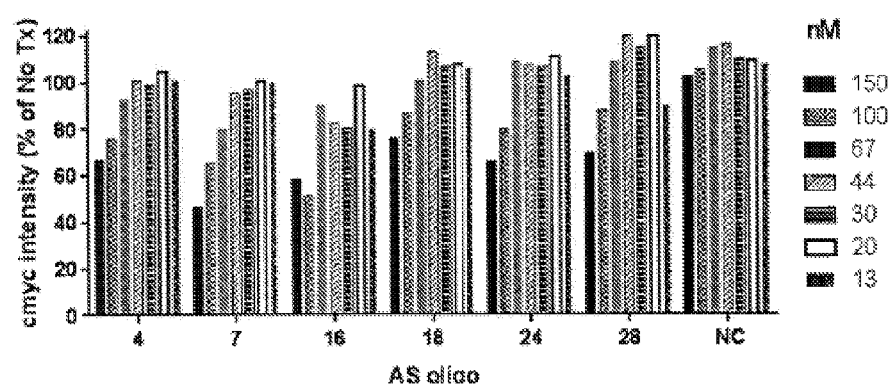
B.
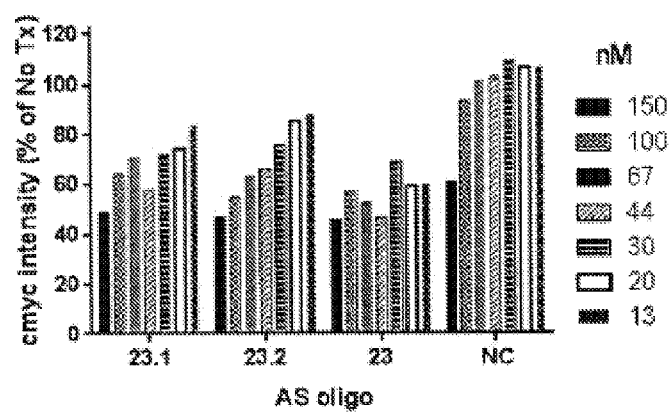

C-MYC ANTISENSE OLIGONUCLEOTIDES AND METHODS FOR USING THE SAME TO TREAT CELL-PROLIFERATIVE DISORDERS

CROSS REFERENCE TO RELATED APPLICATIONS

This application claims priority to U.S. Provisional Patent Application No. 61/719,348, filed Oct. 26, 2012, which is incorporated herein by reference in its entirety.

INCORPORATION BY REFERENCE

The content of the following submission on ASCII text file is incorporated herein by reference in its entirety: a computer readable form (CRF) of the Sequence Listing (file name: 707582000100_Sequence_Listing.txt, date recorded: June 28, 2013, size: 3,159 bytes).

FIELD OF THE INVENTION

This invention relates to antisense c-myc oligonucleotides having specific internucleoside subunit linkages and methods for using the same for the treatment of cancer and other cell proliferative disorders.

BACKGROUND

Cancer is a leading cause of death worldwide. Despite significant advances in the field of chemotherapy, many of the most prevalent forms of cancer still resist chemotherapeutic intervention. Over the past several years, antisense oligodeoxynucleotides (ODNs) have been proposed as therapeutic molecules for the treatment of cancer. Several antisense ODNs targeting a variety of molecules have been shown to have antiproliferative effects against neoplastic cells in vitro and in vivo (Gewirtz, 2000, *J. Clin. Oncol.* 18:1809-1811), and several have demonstrated anti-tumor activity and limited toxicity in Phase I clinical trials (Smith and Wickstrom, 2000, *Methods Enzymol.* 314:537-580). However, use of antisense ODNs for inhibition of gene expression raises several problems, including possible degradation by nucleolytic enzymes and the difficulty antisense ODNs have in crossing biological membranes and entering cells.

The c-myc protein is a member of the helix-loop-helix/leucine zipper (HLH/LZ)1 family of transcription factors that forms heterodimers with Max (Ayer & Eisenman, *Genes Devel.* 7:2110-2119, 1993). In general, trans-activating Myc: Max heterodimers are found in proliferating cells, while trans-repressing Mad:Max heterodimers are found in differentiated cells. C-myc protein level influences cell proliferation, differentiation, and neoplastic transformation, presumably by affecting the balance between Myc:Max and Mad: Max heterodimers (Spencer & Groudine, *Adv. Cancer. Res.* 56:1-48, 1991).

When c-myc protein is overexpressed or is induced at inappropriate times, this balance is perturbed, and cell proliferation and differentiation are disrupted. For example, c-myc overexpression prevents or delays cell differentiation (Coppola & Cole, *Nature* 320:760-763, 1986). It also blocks serum-starved cells from entering the Ga phase of the cell cycle and instead induces them to undergo apoptosis. Overexpression of c-myc has also been implicated in tumor formation in experimental animals and in human patients with Burkitt's lymphoma (Klein, *Genes, Chromosomes, Cancer* 1:3-8, 1989). These and other deleterious consequences of aberrant c-myc expression highlight the importance of proper c-myc gene regulation and how unregulated expression of this gene can result in cell proliferative disorders.

Given the specificity of antisense ODNs toward their mRNA targets and the role played by c-myc overexpression in cancer, what is needed, therefore, is an antisense ODN therapeutic capable of decreasing or eliminating c-myc protein expression in proliferating cells expressing c-myc mRNA and protein.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions and methods for the fabrication and use of c-myc antisense oligonucleotides for the treatment of cell proliferative disorders.

Accordingly, in one aspect, provided herein are oligonucleotides comprising a sequence complementary to an mRNA from a c-myc gene, wherein the nucleoside subunits of the oligonucleotide are joined by intersubunit linkages, wherein at least one of the intersubunit linkages is a thiophosphoramidate linkage, wherein the oligonucleotide is about 6 to about 30 nucleotides, or about 6 to about 20 nucleotides in length, and wherein the oligonucleotide prevents translation of the mRNA by steric hindrance. In some embodiments, about 20% to about 90% of the intersubunit linkages are thiophosphoramidate linkages. In some embodiments, 100% of the intersubunit linkages are thiophosphoramidate linkages.

In other aspects, provided herein are oligonucleotides comprising a sequence complementary to an mRNA from a c-myc gene, wherein the nucleoside subunits of the oligonucleotide are joined by intersubunit linkages, wherein the oligonucleotide comprises alternating thiophosphoramidate or phosphoramidate and thiophosphate or phosphate intersubunit linkages, wherein the oligonucleotide is about 6 to about 30 nucleotides, or about 6 to about 20 nucleotides in length, and wherein the oligonucleotide is a substrate for RNase-H-mediated degradation of the mRNA from a c-myc gene or wherein the oligonucleotide prevents translation of the mRNA by steric hindrance. In some embodiments, the oligonucleotide comprises alternating thiophosphoramidate and thiophosphate linkages. In some embodiments, the oligonucleotide comprises alternating thiophosphoramidate and phosphate linkages. In some embodiments, the oligonucleotide comprises alternating phosphoramidate and thiophosphate linkages. In some embodiments, the oligonucleotide comprises alternating phosphoramidate and phosphate linkages. In some embodiments, the oligonucleotide comprises at least about 45% to 55% thiophosphoramidate linkages. In some embodiments of any of the embodiments herein, the oligonucleotide comprises at least about 45% to 55% phosphoramidate linkages. In some embodiments of any of the embodiments herein, contacting the oligonucleotide with a proliferating cell decreases relative c-myc protein expression in the cell by at least about 50% in comparison to cells that have not been contacted with the oligonucleotide. In some embodiments of any of the embodiments herein, contacting any of the oligonucleotides disclosed herein with a population of proliferating cells decreases the relative cell growth rate of the population of cells by greater than 50% in comparison to cells that have not been contacted with the oligonucleotide.

In other aspects, provided herein are oligonucleotides comprising a sequence complementary to an mRNA from a c-myc gene, wherein the nucleoside subunits of the oligonucleotide are joined by intersubunit linkages, wherein the oligonucleotide comprises two or more contiguous thiophosphoramidate linkages located on both the 5' and 3' ends of the oligonucleotide, wherein the oligonucleotide is about 6 to about 30 nucleotides, or about 6 to about 20 nucleotides in length, and wherein the oligonucleotide is a substrate for RNase-H-mediated degradation of the mRNA from a c-myc gene. In some embodiments, the oligonucleotide further comprises two or more contiguous thiophosphate or phosphate linkages located in between the two or more contiguous thiophosphoramidate linkages located on both the 5' and 3' ends of the oligonucleotide. In some embodiments, the oligonucleotide comprises four contiguous thiophosphoramidate linkages located on the 5' end of the oligonucleotide, five contiguous thiophosphoramidate linkages located on the 3' end of the oligonucleotide, and six contiguous thiophosphate or phosphate linkages located between the four contiguous thiophosphoramidate linkages located on the 5' end of the oligonucleotide and the five contiguous thiophosphoramidate linkages located on the 3' end of the oligonucleotide. In some embodiments of any of the embodiments herein, contacting the oligonucleotide with a proliferating cell decreases relative c-myc protein expression in the cell by at least about 50% in comparison to cells that have not been contacted with the oligonucleotide. In some embodiments of any of the embodiments herein, contacting any of the oligonucleotides disclosed herein with a population of proliferating cells decreases the relative cell growth rate of the population of cells by greater than 50% in comparison to cells that have not been contacted with the oligonucleotide. In some embodiments of any of the embodiments herein, the oligonucleotide is at least 95% complementary to an mRNA from a c-myc gene at the site of the mRNA's translation initiation region. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide comprises the sequence AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), or GTTCTCCTCCTCGTCGCAGT (SEQ ID NO:14).

In other aspects, provided herein are oligonucleotides comprising a sequence complementary to an mRNA from a c-myc gene, wherein the nucleoside subunits of the oligonucleotide are joined by intersubunit linkages, wherein the oligonucleotide comprises two or more contiguous thiophosphoramidate linkages located on both the 5' and 3' ends of the oligonucleotide, wherein the oligonucleotide is about 6 to about 30 nucleotides, or about 6 to about 20 nucleotides in length, and wherein the oligonucleotide is a substrate for RNase-H-mediated degradation of the mRNA from a c-myc gene and/or prevents translation of the mRNA by steric hindrance. In some embodiments, the oligonucleotide further comprises two or more contiguous thiophosphate or phosphate linkages located in between the two or more contiguous thiophosphoramidate linkages located on both the 5' and 3' ends of the oligonucleotide. In some embodiments, the oligonucleotide comprises five contiguous thiophosphoramidate linkages located on the 5' end of the oligonucleotide, four contiguous thiophosphoramidate linkages located on the 3' end of the oligonucleotide, and six contiguous thiophosphate or phosphate linkages located between the five contiguous thiophosphoramidate linkages located on the 5' end of the oligonucleotide and the four contiguous thiophosphoramidate linkages located on the 3' end of the oligonucleotide. In some embodiments of any of the embodiments herein, the oligonucleotide is at least 95% complementary to an mRNA from a c-myc gene at the site of the mRNA's translation initiation region. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide comprises the sequence AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), or GTTCTCCTCCTCGTCGCAGT (SEQ ID NO:14).

In other aspects, provided herein are oligonucleotides comprising a sequence complementary to an mRNA from a c-myc gene, wherein the nucleoside subunits of the oligonucleotide are joined by intersubunit linkages, wherein the oligonucleotide is a substrate for RNase-H-mediated degradation of the mRNA from a c-myc gene, and wherein the oligonucleotide comprises at least two contiguous phosphoramidate intersubunit linkages located on the 5' end of the oligonucleotide; wherein the oligonucleotide comprises at least two contiguous phosphoramidate intersubunit linkages located on the 3' end of the oligonucleotide; wherein the oligonucleotide comprises 2-11 contiguous thiophosphate or phosphate linkages located in between said at least two contiguous phosphoramidate linkages located on the 5' end and said at least two contiguous phosphoramidate linkages located on the 3' end of the oligonucleotide; and wherein the oligonucleotide comprises the sequence AACGTTGAGGGGCAT (SEQ ID NO:1). In some embodiments, contacting the oligonucleotide with a proliferating cell decreases relative c-myc protein expression in the cell by at least about 50% in comparison to cells that have not been contacted with the oligonucleotide. In some embodiments, contacting any of the oligonucleotides disclosed herein with a population of proliferating cells decreases the relative cell growth rate of the population of cells by greater than 50% in comparison to cells that have not been contacted with the oligonucleotide. In some embodiments of any of the embodiments herein, the oligonucleotide further comprises one or more lipid or cholesterol moieties. In some embodiments of any of the embodiments herein, the one or more lipid or cholesterol moieties are connected to the oligonucleotide via a linker. In some embodiments, the one or more lipid or cholesterol moieties is/are located on the 5' end of the oligonucleotide, the 3' end of the oligonucleotide, or both the 5' and 3' ends of the oligonucleotide. In some embodiments the lipid or the cholesterol moiety is located on the 5' end of the oligonucleotide. In some embodiments of any of the embodiments herein, the lipid moiety comprises a Caprylic acid, a Capric acid, a Lauric acid, a Myristic acid, a Palmitic acid, a Stearic acid, a Arachidic acid, a Behenic acid, a Lignoceric acid, or a Cerotic acid. In some embodiments, the lipid moiety comprises a Palmitic acid. In some embodiments, the oligonucleotide further comprises a fluorescent dye label. In some embodiments, the fluorescent dye label is tetramethylrhodamine (TAMRA).

In other aspects, provided herein are pharmaceutical compositions comprising one or more of any of the oligonucleotides disclosed herein. In some embodiments, the pharmaceutical compositions further comprise a pharmaceutically acceptable carrier. In some embodiments of any of the embodiments herein, the composition is formulated for oral, intravenous, subcutaneous, intramuscular, topical, intraperitoneal, intranasal, inhalation, intratumor, or intraocular administration.

In other aspects, provided herein are methods for treating or preventing a cell proliferative disorder in an individual in need thereof comprising: administering to the individual a therapeutically effective amount of one or more of the oligonucleotides disclosed herein or a pharmaceutical composition disclosed herein, wherein administration of one or more of the oligonucleotides relieves at least one symptom of the cell proliferative disorder. In some embodiments, the cell proliferative disorder is cancer. In some embodiments, the cancer is liver cancer or a cancer resulting from B-cell proliferation. In some embodiments of any of the embodiments herein, administration of the therapeutically effective amount of one or more of the oligonucleotides comprises contacting one or more cancer cells with the oligonucleotides. In some embodiments of any of the embodiments herein, administration of the therapeutically effective amount of one or more of the oligonucleotides results in one or more of reduced cellular proliferation, increased apoptosis, or cellular senescence. In some embodiments of any of the embodiments herein, administration of the therapeutically effective amount of one or more of the oligonucleotides does not result in significant toxicity or morbidity in the individual. In some embodiments of any of the embodiments herein, the method further comprises administering to the individual a therapeutically effective amount of one or more additional cancer therapeutic agents. In some embodiments of any of the embodiments herein, the oligonucleotides or the pharmaceutical composition is/are administered orally, intravenously, subcutaneously, intramuscularly, topically, intraperitoneally, intranasaly, intradermally, by inhalation, intratumorally, or intraocularly. In some embodiments of any of the embodiments herein, the individual is human.

In other aspects, provided herein are kits comprising: one or more of the oligonucleotides disclosed herein; and/or one or more of the pharmaceutical compositions disclosed herein.

DESCRIPTION OF THE DRAWINGS

FIG. 3 depicts inhibition of proliferation and Western blot analyses of c-myc protein levels in VAL follicular lymphoma cells treated with anti-c-myc oligonucleotides in vitro. (A). Percentage of relative growth of VAL cells treated with AS ODNs for four days. Cell growth is normalized to untreated controls. (B). Western blot analyses of c-myc protein levels in HepG2 cells treated in vitro with antisense c-myc oligonucleotides, sense controls, or untreated controls for four days versus untreated (Unt) controls. HSP90 was utilized as a loading control and relative protein expression was normalized versus untreated controls.

FIG. 4 depicts c-myc antisense ODN effects on HepG2 tumor cell growth in an in vivo tumor prevention model. Tumor volumes (A) at indicated times and tumor weight (B) at 63 days following 2 weeks treatment initiated at day 47 of the experiment are shown for mice treated with c-myc antisense ODN, sense ODN control, or PBS-treated controls.

FIG. 5 depicts c-myc antisense ODN effects on VAL tumor cell growth in an in vivo tumor regression model. Tumor volumes (A) at indicated times and tumor weight (B) at 27 days following 2 weeks treatment initiated at day 13 in mice treated with c-myc antisense ODN, sense ODN control, or PBS-treated controls.

FIG. 13 depicts immunofluorescence levels of c-myc protein in HepG2 cells treated in vitro with antisense c-myc oligonucleotides and a non-silencing control (NC) from Example 5.

DETAILED DESCRIPTION OF THE INVENTION

Figure 1:
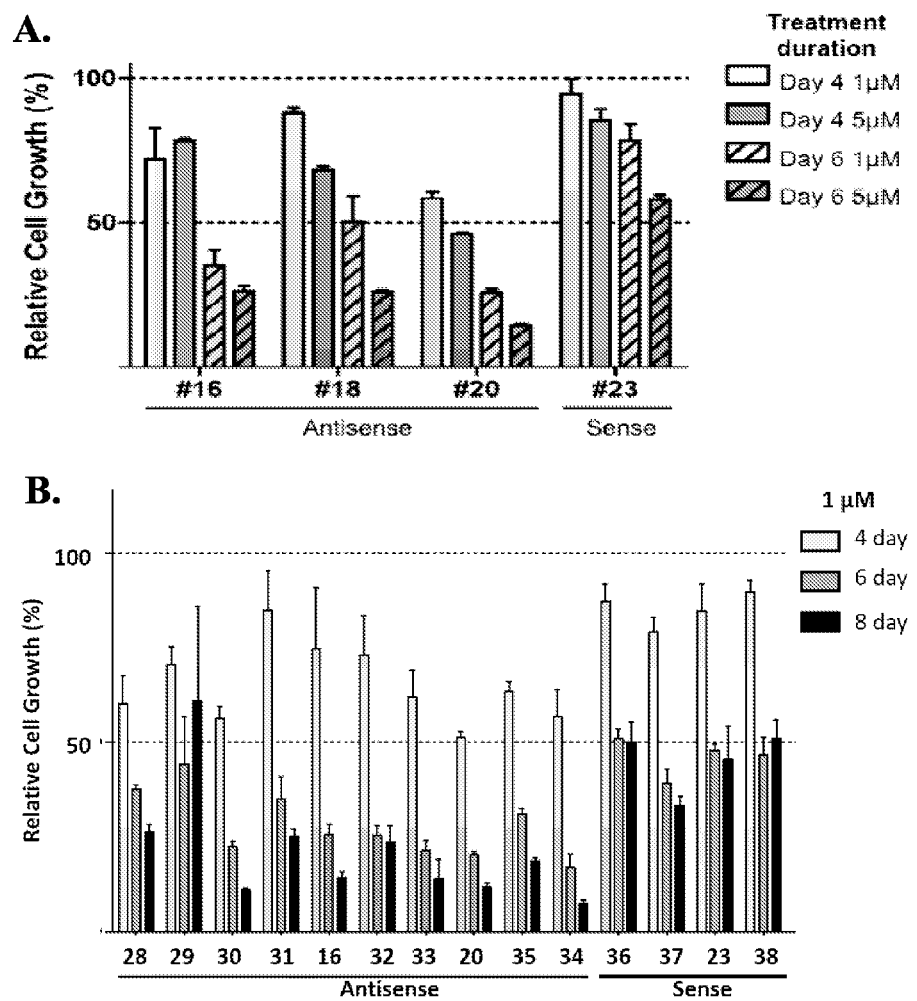
FIG. 1 depicts inhibition of proliferation of HepG2 liver cancer cells due to anti-c-myc oligonucleotides in vitro. (A). Percentage of relative growth of HepG2 cells treated with AS ODNs for four or six days. (B). Percentage of relative growth of HepG2 cells treated with AS ODNs for four, six, or eight days. Cell growth is normalized to untreated controls.

This invention provides, inter alia, antisense oligonucleotides that can effectively prevent or decrease c-myc protein expression as well as decrease overall rates of cell proliferation in in vitro and mammalian in vivo models of cell proliferative disorders as well as methods for using the same. The inventors have discovered, inter alia, that antisense oligonucleotides having specific internucleoside linkages arrayed within the oligonucleotides can effectively prevent or decrease c-myc mRNA translation into protein within cells by sterically inhibiting the translation of the c-myc message into protein, by causing RNAse H-mediated degradation of the c-myc mRNA, or through steric inhibition and/or causing RNAse H-mediated degradation of the c-myc mRNA.

I. General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; Komberg and Baker, *DNA Replication,* 2nd Ed. (Freeman, San Francisco, 1992); Scheit, *Nucleotide Analogs* (John Wiley, New York, 1980); Uhlmann and Peyman, *Chemical Reviews,* 90:543-584, 1990.

II. Definitions

The term "nucleoside" refers to a moiety having the general structure represented below, where B represents a nucleobase and the 2' carbon can be substituted as described below. When incorporated into an oligomer or polymer, the 3' carbon is further linked to an oxygen or nitrogen atom.

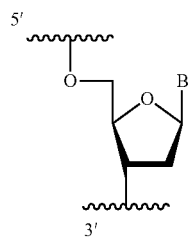

This structure includes 2'-deoxy and 2'-hydroxyl (i.e. deoxyribose and ribose) forms, and analogs. Less commonly, a 5'-NH group can be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, and further analogs. Such analogs are typically designed to affect binding properties, e.g., stability, specificity, or the like.

A "polynucleoside," "oligonucleoside," "polynucleotide," or "oligonucleotide" can be used interchangeably herein to refer to an oligomer or polymer of the above-referenced nucleoside moieties, having between about 6 and about 20 such moieties, joined by specific internucleoside linkages between their 5' and 3' positions. These terms "oligonucleotide" and "oligonucleoside" also include such polymers or oligomers having modifications, known to one skilled in the art, to the sugar (e.g., 2' substitutions), the base (see the definition of "nucleobase" below), as well as the 3' and 5' termini.

The term "internucleoside linkage" refers to phosphorus-based linkages two atoms in length between the 5' oxygen and 3' carbon in the structure above, with phosphorus linking the 5' oxygen to a nitrogen or oxygen atom on the 3' carbon. Such linkages include, but are not limited to, phosphodiester or phosphate (i.e. a "native" linkage), phosphotriester, methylphosphonate, P3'→N5' phosphoramidate, N3'→P5' phosphoramidate (NP), N3'→P5' thiophosphoramidate (NPS), and phosphorothioate linkages. Such linkages can be the same or different within a molecule.

An "NPS linkage" in the compounds of the invention is the group 3'-NH—P(O)(S$^-$)-5'; an "NP linkage" is the group 3'-NH—P(O)(O$^-$)-5'.

A "nucleobase" (or "base") includes (i) native DNA and RNA nucleobases (uracil, thymine, adenine, guanine, and cytosine), (ii) modified nucleobases or nucleobase analogs (for example, but not limited to, 5-methylcytosine, 5-bromouracil, or inosine) and (iii) nucleobase analogs. A "nucleobase analog" is a compound whose molecular structure is similar that of a typical DNA or RNA nucleobase.

The term "lipid" encompasses substances that are soluble in organic solvents, but sparingly soluble, if at all, in water. The term lipid includes, but is not limited to, hydrocarbons, oils, fats (such as fatty acids and glycerides), sterols (for example, cholesterol), steroids and derivative forms of these compounds. In some embodiments, lipids are hydrocarbons, fatty acids and their derivatives. Fatty acids usually contain even numbers of carbon atoms in a straight chain (commonly 12-24 carbons) and can be saturated or unsaturated, and can contain, or be modified to contain, a variety of substituent groups. For simplicity, the term "fatty acid" also encompasses fatty acid derivatives, such as fatty acid esters.

The term "substituted" refers to a compound which has been modified by the exchange of one atom or moiety for another, typically substitution of hydrogen by a different atom or moiety.

The term "RNA target" refers to an RNA transcript to which an antisense oligonucleotide binds in a sequence specific manner. In some embodiments the RNA target is one or more c-myc mRNA molecules.

As used herein, "RNAse H-mediated degradation" refers to the specific cleavage of the 3'-O—P bond of an RNA in a DNA/RNA duplex to produce 3'-hydroxyl and 5'-phosphate terminated products by the nonspecific endogenous cellular ribonuclease RNAse H.

As used herein, the term "gapmer" refers to an oligonucleotide comprising two end regions (the "5' end" and the "3' end") and a central region (a "gap"), wherein the 5' end and the 3' end regions comprise at least one modification difference compared to the gap region. Such modifications include monomeric linkage and sugar modifications as well as the absence of modification (unmodified RNA or DNA). Thus, in certain embodiments, the nucleotide linkages in each of the 5' and 3' ends are different than the nucleotide linkages in the gap. In certain embodiments, the modifications in the 5' and 3' ends are the same as one another. In certain embodiments, the modifications in the 5' and 3' ends are different from each other. In certain embodiments, nucleotides in the gap are unmodified and nucleotides in the 5' and 3' ends are modified. In certain embodiments, the modification(s) within each 5' and 3' end are the same. In certain embodiments, the modification(s) in one of the 5' or 3' ends are different from the modification(s) in the other end. In some embodiments, gapmer oligonucleotide hybridization to a target mRNA molecule (such as a c-myc mRNA molecule), results in the RNAse H-mediated degradation of the target mRNA molecule.

As used herein, an antisense oligonucleotide that prevents target mRNA translation by "steric hindrance" is an oligonucleotide that interferes with gene expression or other mRNA-dependent cellular processes (for example, mRNA splicing or initiation of translation at the level of the ribosome) by binding to a target mRNA. Such an oligonucleotide may or may not be RNase-H independent in functionality.

An "individual" can be a mammal, such as any common laboratory model organism, or a mammal. Mammals include, but are not limited to, humans and non-human primates, farm animals, sport animals, pets, mice, rats, and other rodents. In some embodiments, an individual is a human.

As used herein, "treatment" (and grammatical variations thereof such as "treat" or "treating") refers to clinical intervention designed to alter the natural course of the individual or cell being treated during the course of clinical pathology. Desirable effects of treatment include, but are not limited to, decreasing the rate of disease progression, amelioration or palliation of the disease state, and remission or improved prognosis.

As used herein, "prevention" includes providing prophylaxis with respect to occurrence or recurrence of a disease or the symptoms associated with a disease in an individual. An individual may be predisposed to, susceptible to, or at risk of developing a disease, but has not yet been diagnosed with the disease.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect. For an antisense oligomer, this effect is typically brought about by inhibiting translation or natural splice-processing of a selected target sequence.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. C-myc Antisense Oligonucleotides

The principle underlying antisense technology lies in the ability of an antisense oligonucleotide to hybridize to a target nucleic acid and modulate gene expression, such as by affecting transcription, translation, or splicing. This modulation of gene expression can specifically be achieved by, for example, target degradation, occupancy-based inhibition (i.e. sterics), or a combination of both. An example of modulation of RNA target function by degradation is RNase H-based degradation of the target RNA upon hybridization with a DNA-like antisense compound. Another example is interference with mRNA translation due to steric hindrance. This sequence-specificity makes antisense oligonucleotides attractive as therapeutics to selectively modulate the expression of genes involved in the pathogenesis of any one of a variety of diseases (such as cell proliferative disorders). Antisense technology is an effective means for reducing the expression of one or more specific gene products and can therefore prove to be uniquely useful in a number of therapeutic applications.

The sequence of any of the antisense oligonucleotides disclosed herein can be, but need not necessarily be, 100% complementary to an mRNA from a c-myc gene to be specifically hybridizable. In one embodiment, the antisense oligonucleotides of the present invention comprise at least 70%, or at least 75%, or at least 80%, or at least 85% sequence complementarity to an mRNA from a c-myc gene. In other embodiments, the antisense oligonucleotides of the present invention comprise at least 90% sequence complementarity and even comprise at least 95% or at least 99% sequence complementarity to an mRNA from a c-myc gene to which they are targeted. For example, an antisense oligonucleotide in which 18 of 20 nucleobases of the antisense oligonucleotide are complementary to an mRNA from a c-myc gene, would specifically hybridize and would represent 90 percent complementarity. In this example, the remaining noncomplementary nucleobases can be clustered or interspersed with complementary nucleobases and need not be contiguous to each other or to complementary nucleobases. Percent complementarity of an antisense compound with a region of a target nucleic acid can be determined routinely using BLAST programs (basic local alignment search tools) and PowerBLAST programs known in the art (Altschul et al., *J. Mol. Biol*, 1990, 215, 403-410; Zhang & Madden, *Genome Res.*, 1997, 7, 649-656).

Provided herein are antisense c-myc oligonucleotides having specific internucleoside subunit linkages wherein the oligonucleotides effectively decrease or prevent c-myc protein expression within proliferating cells. In some aspects, the c-myc antisense oligonucleotides decrease or prevent translation of an mRNA from a c-myc gene by steric hindrance. In other aspects, the c-myc antisense oligonucleotides decrease or prevent translation of an mRNA from a c-myc gene by RNase-H-mediated degradation of the mRNA from a c-myc gene. In yet other aspects, the c-myc antisense oligonucleotides decrease or prevent translation of an mRNA from a c-myc gene by steric hindrance and/or by RNase-H-mediated degradation of the mRNA from a c-myc gene. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide.

In some aspects of any of the c-myc antisense oligonucleotides disclosed herein, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length. In one embodiment, the c-myc antisense oligonucleotides is at least about 6 to at least about 50, including at least about 8 to at least about 30, is about 6 to about 30 nucleotides, or is about 6 to about 20, or at least about 10 to at least about 20, and at least about 12 to at least about 16 nucleotides in length. In some embodiments, any of the c-myc antisense oligonucleotides disclosed herein are modified with one or more lipid and/or cholesterol moieties. In some embodiments, the cholesterol and/or lipid moiety is attached to the oligonucleotide via a linking group. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14). In other embodiments, the oligonucleotide comprises the sequence AACGTTGAGGGGCAT (SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

Methods known in the art can be used to determine whether a c-myc antisense oligonucleotide is effective in preventing or decreasing expression of c-myc in a proliferating cell. These include, without limitation, methods to assess mRNA such as reverse transcription-quantitative PCT (RT-qPCR), Northern Blot, in situ hybridization, microarray, serial analysis of gene expression (SAGE), or RNA-Seq. Also included are common methods known in the art to assess c-myc protein levels in proliferating cells such as, but not limited to, Western Blot, immunohistochemistry, enzyme-linked immunosorbant assay (ELISA), radioimmunoassay (RIA), or 2D gel electrophoresis followed by quantitative mass spectrometry.

A. Internucleoside Subunit Linkages

In some aspects, any of the c-myc antisense oligonucleotides useful in this invention include oligonucleotides containing modified backbones or non-natural internucleoside linkages. As defined herein, oligonucleotides having modified backbones include, inter alia, those that retain a phosphorus atom in the backbone of the oligonucleotide.

In some embodiments, the modified intersubunit linkages found in any of the c-myc antisense oligonucleotides disclosed herein include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiophosphoramidates, thionoalkylphosphonates, thionoalkylphosphotriesters, thiophosphates, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Methods for synthesizing these modified intersubunit linkages can be found in U.S. Pat. Nos. 5,177,196; 5,188,897; 5,264,423; 5,276,019; 5,278,302; 5,286,717; 5,321,131; 5,399,676; 40 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein in their entirety.

In some embodiments, the modified intersubunit linkages found in any of the c-myc antisense oligonucleotides disclosed herein are thiophosphoramidate (NPS), phosphoramidate (NP), thiophosphate (PS) linkages, and phosphodiester (i.e. a phosphate) (PO). An NPS linkage in the oligonucleotides of the present invention is the group 3'-NH—P(O)(S—)-5'. An NP linkage is the group 3'-NH—P(O)(O—)-5'. A PS linkage is the group 3'-O—P(O)(S—)-5'. A phosphodiester linkage is the group $PO_3$. In particular, NPS and NP linkages have the benefits of high hydrolytic stability and resistance to cellular nucleases. In addition, they show much less nonspecific protein binding than exhibited by PS linkages. Methods for synthesizing NP intersubunit linkages can be found in U.S. Pat. Nos. 5,837,835; and 5,824,793; and NPS intersubunit linkages in U.S. Pat. Nos. 5,824,793; and 5,859,233, the disclosures of which are incorporated by reference herein in their entirety.

B. Antisense ODN Inhibitors of c-Myc Protein Expression by Steric Hindrance

For oligonucleotides that prevent target mRNA translation via a steric-acting mechanism, oligonucleotide-target mRNA heteroduplex formation does not lead to RNA turnover (as is the case with RNAse-H mediated degradation), but results instead in the hindrance of RNA processing, nucleocytoplasmic transport or translation of the mRNA itself at the level of the ribosome. This is particularly the case when the antisense oligonucleotide is targeted to the translation initiation region of the target mRNA (i.e. the region on and surrounding the START codon).

Accordingly, in some aspects, provided herein are oligonucleotides comprising a sequence complementary to an mRNA from a c-myc gene, wherein the nucleoside subunits of the oligonucleotide are joined by intersubunit linkages, wherein at least one of the intersubunit linkages is a thiophosphoramidate linkage, wherein the oligonucleotide is about 6 to about 25 nucleotides in length, and wherein the oligonucleotide prevents translation of the mRNA by steric hindrance. In one embodiment, the oligonucleotide is about 6 to about 20 nucleotides or is about 6 to about 30 nucleotides in length.

In some embodiments, the c-myc antisense oligonucleotide that prevents translation of an mRNA from a c-myc gene due to steric hindrance contains at least one thiophosphoramidate (NPS) intersubunit linkage. In other embodiments, the oligonucleotide contains any of 6, 7, 8, 9, 10, 11, 12, 13, 14, 15, 16, 17, 18, 19, 20, 21, 22, 23, 24, or 25 NPS intersubunit linkages, or up to about 25, or 30, or 50 NPS intersubunit linkages. In another embodiment, the oligonucleotide comprises 6, 7, 8, 9, 10, 11, 12, 13, 14, 15, 16, 17, 18, 19, 20, 21, 22, 23, 24, or 25 NPS intersubunit linkages. In yet other embodiments, the oligonucleotide contains at least about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%, inclusive, including any percentages in between these values, NPS intersubunit linkages. In further embodiments, about 10% to about 95%, about 20% to about 90%, about 30% to about 80%, about 40% to about 70%, or about 50% of the intersubunit linkages are thiophosphoramidate linkages. In one embodiment, about 10% to about 90% of the intersubunit linkages are thiophosphoramidate linkages. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments, the oligonucleotide has a sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), and TTTCATTGTTTTCCA (SEQ ID NO:4). In other embodiments, the oligonucleotide comprises the sequence AACGTTGAGGGGCAT (SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

In other aspects, provided herein are oligonucleotides comprising a sequence complementary to an mRNA from a c-myc gene, wherein the nucleoside subunits of the oligonucleotide are joined by intersubunit linkages, wherein at least one of the intersubunit linkages is a phosphoramidate linkage, wherein the oligonucleotide is about 6 to about 25 nucleotides in length, and wherein the oligonucleotide prevents translation of the mRNA by steric hindrance. In one embodiment, the oligonucleotide is about 6 to about 20 nucleotides or is about 6 to about 30 nucleotides in length. In some embodiments, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length. In one embodiment, the c-myc antisense oligonucleotide is at least about 6 to at least about 50, including at least about 8 to at least about 30, about 6 to about 20 nucleotides or about 6 to about 30 nucleotides or at least about 10 to at least about 20, and at least about 12 to at least about 16 nucleotides in length.

In some embodiments, the c-myc antisense oligonucleotide that prevents translation of an mRNA from a c-myc gene due to steric hindrance contains at least one phosphoramidate (NP) intersubunit linkage. In other embodiments, the oligonucleotide contains any of 6, 7, 8, 9, 10, 11, 12, 13, 14, 15, 16, 17, 18, 19, 20, 21, 22, 23, 24, or 25 NP intersubunit linkages, or up to about 25, or 30, or 50 NP intersubunit linkages. In another embodiment, the oligonucleotide comprises 6, 7, 8, 9, 10, 11, 12, 13, 14, 15, 16, 17, 18, 19, 20, 21, 22, 23, 24, or 25 NP intersubunit linkages. In yet other embodiments, the oligonucleotide contains at least about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%, inclusive, including any percentages in between these values, NP intersubunit linkages. In further embodiments, about 10% to about 90%, about 20% to about 80%, about 30% to about 70%, about 40% to about 60%, or about 50% of the intersubunit linkages are phosphoramidate linkages. In one embodiment, about 10% to about 90% of the intersubunit linkages are phosphoramidate linkages. In some embodiments, the oligonucleotide is complementary to an mRNA from a c-myc gene at the site of the mRNA's translation initiation region. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14). In other embodiments, the oligonucleotide comprises the sequence AACGTTGAGGGGCAT (SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

In other embodiments, the c-myc antisense oligonucleotide that prevents translation of an mRNA from a c-myc gene due to RNase-H-mediated degradation of the mRNA from a c-myc gene and/or steric hindrance is fluorescently labeled. Non-limiting examples of fluorescent labels include fluorescein, phosphor, rhodamine, and polymethine dye derivative. Examples of commercially available fluorescent dyes include BODIPY FL (brand name, manufactured by Molecular Probe Inc.), FluorePrime (trade name, manufactured by Amersham Pharmacia), Fluoredite (trade name, manufactured by Millipore Corporation), FAIL (manufactured by ABI), Cy3 and Cy5 (manufactured by Amersham Pharmacia), and tetramethylrhodamine (TAMRA; manufactured by Molecular Probe Inc.).

Techniques for synthesizing oligonucleotides with NPS, NP, PS, or PO intersubunit linkages can be found, inter alia, in U.S. Pat. No. 7,494,982, the disclosure of which is incorporated herein in its entirety.

In some embodiments, the c-myc antisense oligonucleotide that prevents translation of an mRNA from a c-myc gene due to steric hindrance is an oligonucleotide shown in Table 1.

TABLE 1

Steric blocking c-myc antisense oligonucleotides

| ODN # | 5'-d-(Oligonucleotide)-3' | SEQ ID NO: | Type of intersubunit linkage | Mode of action |
|---|---|---|---|---|
| 2 | AACGTTGAGGGGCAT | 1 | All-NP | steric blocker |
| 13 | Palm-AACGTTGAGGGGCAT | 1 | All-NP | steric blocker |
| 15 | TAACGTTGAGGGGCAT | 3 | All-NPS | steric blocker |
| 29 | TAACGTTGAGGGGCAT-TAMRA | 3 | All-NP | steric blocker |

TABLE 1-continued

Steric blocking c-myc antisense oligonucleotides

| ODN # | 5'-d-(Oligonucleotide)-3' | SEQ ID NO: | Type of intersubunit linkage | Mode of action |
|---|---|---|---|---|
| 30 | Palm-AACGTTGAGGGGCAT-TAMRA | 1 | All-NP | steric blocker |
| 31 | Palm-AACGTTGAGGGGCAT-TAMRA | 1 | All-NPS | steric blocker |

*Palm = Palmitic acid lipid moiety (see discussion infra);
**TAMRA = fluorescent label C. Antisense ODN Inhibitors of c-Myc Protein Expression by RNAse-H Mediated Degradation Following heteroduplex formation with a target mRNA, certain antisense oligonucleotides (i.e. gapmers) can serve as a substrate for the intracellular ribonuclease RNase H, which leads to cleavage of the target mRNA component of the heteroduplex. While not intending to be bound by theory, it is thought that once the target mRNA is cleaved, the gapmer oligonucleotides can target additional copies of the target mRNA. Gapmers are chimeric oligonucleotides comprising a central region (a "gap") and a region on either side of the central region (the "5' end" and the "3' end"), wherein the nucleoside subunits contained within the gap comprise at least one modification difference in comparison to the nucleoside subunits that make up the 5' and "3' ends.

Accordingly, in some aspects, provided herein are oligonucleotide comprising a sequence complementary to an mRNA from a c-myc gene, wherein the nucleoside subunits of the oligonucleotide are joined by intersubunit linkages, wherein the oligonucleotide comprises two or more contiguous thiophosphoramidate or phosphoramidate linkages located on both the 5' and 3' ends of the oligonucleotide, wherein the oligonucleotide is about 6 to about 25 nucleotides in length, and wherein the oligonucleotide is a substrate for RNase-H-mediated degradation of the mRNA from a c-myc gene In one embodiment, the oligonucleotide is about 6 to about 20 nucleotides or is about 6 to about 30 nucleotides in length. In some embodiments, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length. In one embodiment, the c-myc antisense oligonucleotide is at least about 6 to at least about 50, including at least about 8 to at least about 30, is about 6 to about 20 nucleotides or is about 6 to about 30 nucleotides or at least about 10 to at least about 20, and at least about 12 to at least about 16 nucleotides in length. In another embodiment, the oligonucleotide comprises two or more contiguous thiophosphoramidate linkages located on both the 5' and 3' ends of the oligonucleotide. In yet a further embodiment, the oligonucleotide comprises two or more contiguous phosphoramidate linkages located on both the 5' and 3' ends of the oligonucleotide. In still a further embodiment, the oligonucleotide further comprises two or more contiguous thiophosphate or phosphate linkages located in between (i.e., in the gap between) the two or more contiguous thiophosphoramidate linkages located on both the 5' and 3' ends of the oligonucleotide.

In some embodiments, the c-myc antisense oligonucleotides that prevent translation of an mRNA from a c-myc gene due to RNase-H-mediated degradation of the mRNA from a c-myc gene provided herein comprise at least about 6, 7, 8, 9, 10, 11, 12, 13, 14, 15, 16, 17, 18, 19, 20, 21, 22, 23, 24, or 25 nucleotides in length having a gap of about 2 to 16 nucleotides in length and having 5' and 3' end regions that are independently at least 2 to 16 nucleotides in length. Exemplary 5' end-gap-3'end configurations for the c-myc antisense gapmer oligonucleotides disclosed herein are 2-4-2, 2-5-2, 4-6-4, 3-6-3, 2-6-2, 4-7-4, 3-7-3, 2-7-2, 4-8-4, 3-8-3, 2-8-2, 2-9-2, 2-10-2, 2-14-2, 2-13-3, 3-13-2, 2-12-4, 4-12-2, 3-12-3, 2-11-5, 5-11-2, 3-11-4, 4-11-3, 2-15-2, 2-14-3, 3-14-2, 2-13-4, 4-13-2, 3-13-3, 2-12-5, 5-12-2, 3-12-4, 4-12-3, 2-11-6, 6-11-2, 3-11-5, 5-11-3, 4-11-4, 2-16-2, 2-15-3, 3-15-2, 2-14-4, 4-14-2, 3-14-3, 2-13-5, 5-13-2, 3-13-4, 4-13-3, 2-12-6, 6-12-2, 3-12-5, 5-12-3, 4-12-4, 2-11-7, 7-11-2, 3-11-6, 6-11-3, 4-11-5, 5-11-4, 2-16-2, 2-15-3, 3-15-2, 2-14-4, 4-14-2, 3-14-3, 2-13-5, 5-13-2, 3-13-4, 4-13-3, 2-12-6, 6-12-2, 3-12-5, 5-12-3, 4-12-4, 2-11-7, 7-11-2, 3-11-6, 6-11-3, 4-11-5, 5-11-4, 2-17-2, 2-16-3, 3-16-2, 2-15-4, 4-15-2, 3-15-3, 2-14-5, 5-14-2, 3-14-4, 4-14-3, 2-13-6, 6-13-2, 3-13-5, 5-13-3, 4-13-4, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 2-18-2, 2-17-3, 3-17-2, 2-16-4, 4-16-2, 3-16-3, 2-15-5, 5-15-2, 3-15-4, 4-15-3, 2-14-6, 6-14-2, 3-14-5, 5-14-3, 4-14-4, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 2-19-2, 2-18-3, 3-18-2, 2-17-4, 4-17-2, 3-17-3, 2-16-5, 5-16-2, 3-16-4, 4-16-3, 2-15-6, 6-15-2, 3-15-5, 5-15-3, 4-15-4, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 2-20-2, 2-19-3, 3-19-2, 2-18-4, 4-18-2, 3-18-3, 2-17-5, 5-17-2, 3-17-4, 4-17-3, 2-16-6, 6-16-2, 3-16-5, 5-16-3, 4-16-4, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6.

In some embodiments, the c-myc antisense oligonucleotide that prevents translation of an mRNA from a c-myc gene due to RNase-H-mediated degradation of the mRNA from a c-myc gene comprises four contiguous thiophosphoramidate linkages located on the 5' end of the oligonucleotide, five contiguous thiophosphoramidate linkages located on the 3' end of the oligonucleotide, and six contiguous thiophosphate or phosphate linkages located between the four contiguous thiophosphoramidate linkages located on the 5' end of the oligonucleotide and the five contiguous thiophosphoramidate linkages located on the 3' end of the oligonucleotide. In some embodiments, the c-myc antisense oligonucleotide comprises four contiguous phosphoramidate linkages located on the 5' end of the oligonucleotide, five contiguous phosphoramidate linkages located on the 3' end of the oligonucleotide, and six contiguous thiophosphate or phosphate linkages located between the four contiguous phosphoramidate linkages located on the 5' end of the oligonucleotide and the five contiguous phosphoramidate linkages located on the 3' end of the oligonucleotide. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments, the oligonucleotide is complementary to an mRNA from a c-myc gene at the site of the mRNA's translation initiation region. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14), In other embodiments, the oligonucleotide comprises the sequence AACGTTGAGGGGCAT (SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

In other aspects, also provided herein are oligonucleotides comprising a sequence complementary to an mRNA from a c-myc gene, wherein the nucleoside subunits of the oligonucleotide are joined by intersubunit linkages, wherein the oligonucleotide is a substrate for RNase-H-mediated degradation of the mRNA from a c-myc gene, and wherein the oligonucleotide comprises at least two contiguous phosphoramidate intersubunit linkages located on the 5' end of the oligonucleotide; wherein the oligonucleotide comprises at least two contiguous phosphoramidate intersubunit linkages located on the 3' end of the oligonucleotide; wherein the oligonucleotide comprises 2-11 contiguous thiophosphate or phosphate linkages located in between said at least two contiguous phosphoramidate linkages located on the 5' end and said at least two contiguous phosphoramidate linkages located on the 3' end of the oligonucleotide; and wherein the oligonucleotide comprises the sequence AACGTTGAGGGGCAT (SEQ ID NO:1). In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14) In other embodiments, the oligonucleotide comprises the sequence AACGTTGAGGGGCAT(SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

Techniques for synthesizing oligonucleotides with varying types of intersubunit linkages can be found, inter alia, in U.S. Pat. No. 7,494,982, the disclosure of which is incorporated herein in its entirety.

In other embodiments, the c-myc antisense oligonucleotide that prevents translation of an mRNA from a c-myc gene due to RNase-H-mediated degradation of the mRNA from a c-myc gene and/or steric hindrance is fluorescently labeled. Non-limiting examples of fluorescent labels include fluorescein, phosphor, rhodamine, and polymethine dye derivative. Examples of commercially available fluorescent dyes include BODIPY FL (brand name, manufactured by Molecular Probe Inc.), FluorePrime (trade name, manufactured by Amersham Pharmacia), Fluoredite (trade name, manufactured by Millipore Corporation), FAIL (manufactured by ABI), Cy3 and Cy5 (manufactured by Amersham Pharmacia), and tetramethylrhodamine (TAMRA; manufactured by Molecular Probe Inc.).

In some embodiments, the c-myc antisense oligonucleotide that prevents translation of an mRNA from a c-myc gene due to RNAse H-mediated degradation of the mRNA is an oligonucleotide shown in Table 2.

TABLE 2

Gapmer c-myc antisense oligonucleotides

| ODN # | 5'-d-(Oligonucleotide)-3' | SEQ ID NO: | Type of intersubunit linkage(s) | Mode of action |
|---|---|---|---|---|
| 16 | Palm-AACGTTGAGGGGCAT | 1 | NPS/PS/NPS | RNAse-H |
| 17 | TAACGTTGAGGGGCAT | 3 | NPS/PS/NPS | RNAse-H |
| 20 | Palm-AACGTTGAGGGGCAT | 1 | NP/PS/NP | RNAse-H |
| 21 | TAACGTTGAGGGGCAT | 3 | NP/PS/NP | RNAse-H |
| 32 | Palm-AACGTTGAGGGGCAT-TAMRA | 1 | NPS/PS/NPS | RNAse-H |
| 33 | TAACGTTGAGGGGCAT-TAMRA | 3 | NPS/PS/NPS | RNAse-H |
| 35 | TAACGTTGAGGGGCAT-TAMRA | 3 | NP/PS/NP | RNAse-H |

*Palm = palmitic acid lipid moiety (see discussion infra);
**TAMRA = fluorescent label;
***underlined and bold nucleotides indicate a different intersubunit linkage D. Antisense ODN Inhibitors of c-Myc Protein Expression by Steric Hindrance and/or RNAse H-Mediated Degradation Provided herein are c-myc antisense oligonucleotides that can effectively prevent or decrease c-myc mRNA translation into protein within cells through steric inhibition and/or RNAse H-mediated degradation. These oligonucleotides possess characteristics of both traditional steric-blocking antisense oligonucleotides as well as gapmers, which cause RNAse H-mediated degradation of target mRNA.

Accordingly, provided herein are antisense oligonucleotides comprising a sequence complementary to an mRNA from a c-myc gene, wherein the nucleoside subunits of the oligonucleotide are joined by intersubunit linkages, wherein the oligonucleotide comprises alternating thiophosphoramidate or phosphoramidate and thiophosphate or phosphate intersubunit linkages, wherein the oligonucleotide is about 6 to about 25 nucleotides in length, and wherein the oligonucleotide is a substrate for RNase-H-mediated degradation of the mRNA from a c-myc gene and/or wherein the oligonucleotide prevents translation of the mRNA by steric hindrance. In one embodiment, the oligonucleotide is about 6 to about 20 nucleotides or is about 6 to about 30 nucleotides in length. In some embodiments, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length. In one embodiment, the c-myc antisense oligonucleotide is at least about 6 to at least about 50, including at least about 8 to at least about 30, or is about 6 to about 20 nucleotides or is about 6 to about 30 nucleotides or at least about 10 to at least about 20, and at least about 12 to at least about 16 nucleotides in length.

In some embodiments, the c-myc antisense oligonucleotides that prevent translation of an mRNA from a c-myc gene due to RNase-H-mediated degradation of the mRNA and/or steric hindrance (such as any of the oligonucleotides provided herein) are at least about 6, 7, 8, 9, 10, 11, 12, 13, 14, 15, 16, 17, 18, 19, 20, 21, 22, 23, 24, or 25 nucleotides in length and comprise the sequence $(A_nB_y)_qA_n$. In some embodiments, A comprises a thiophosphoramidate or phosphoramidate intersubunit linkage, B comprises a thiophosphate or phosphate intersubunit linkage, n and y indicate independently the number of contiguous intersubunit linkages represented by A and B, respectively, and q is any number from 1-10. In one embodiment, n and y are both 1 and the oligonucleotide is any of at least about 7, 9, 11, 13, 15 nucleotides in length. In another embodiment, n is 1 and y is 2 and the oligonucleotide is any of at least about 7, 10, 13, 16, 19, 22, 25 nucleotides in length. In another embodiment, n is 1 and y is 3 and the oligonucleotide is any of at least about 5, 9, 13, 17, nucleotides in length. In another embodiment, n is 1 and y is 4 and the oligonucleotide is any of at least about 6, 12, 18, or 24 nucleotides in length. In another embodiment, n is 1 and y is 5 and the oligonucleotide is any of at least about 7, 14, or 21 nucleotides in length. In another embodiment, n is 1 and y is 6 and the oligonucleotide is any of at least about 8, 16, 24 nucleotides in length. In another embodiment, n is 1 and y is 7 and the oligonucleotide is any of at least about 9 or 17 nucleotides in length. In another embodiment, n is 1 and y is 8 and the oligonucleotide is any of at least about 10 or 20 nucleotides in length. In another embodiment, n is 2 and y is 1 and the oligonucleotide is any of at least about 8, 11, 14, 17, nucleotides in length. In another embodiment, n is 3 and y is 1 and the oligonucleotide is any of at least about 7, 11, 15, nucleotides in length.

In one embodiment, n and y are both 2 and the oligonucleotide is any of at least about 6, 12, 18, or 24 nucleotides in length. In another embodiment, n is 2 and y is 3 and the oligonucleotide is any of at least about 7, 14, or 21 nucleotides in length. In another embodiment, n is 2 and y is 4 and the oligonucleotide is any of at least about 8, 16, or 24 nucleotides in length. In another embodiment, n is 2 and y is 5 and the oligonucleotide is any of at least about 9 or 18 nucleotides in length. In another embodiment, n is 2 and y is 6 and the oligonucleotide is any of at least about 10 or 20 nucleotides in length. In another embodiment, n is 2 and y is 7 and the oligonucleotide is any of at least about 11 or 22 nucleotides in length. In another embodiment, n is 3 and y is 2 and the oligonucleotide is any of at least about 8, 16, or 24 nucleotides in length. In another embodiment, n is 4 and y is 2 and the oligonucleotide is any of at least about 10 or 20 nucleotides in length. In another embodiment, n is 5 and y is 2 and the oligonucleotide is any of at least about 11 or 22 nucleotides in length.

In one embodiment, n and y are both 3 and the oligonucleotide is any of at least about 9 or 18 nucleotides in length. In another embodiment, n is 3 and y is 4 and the oligonucleotide is any of at least about 10 or 20 nucleotides in length. In another embodiment, n is 3 and y is 5 and the oligonucleotide is any of at least about 11 or 22 nucleotides in length. In another embodiment, n is 3 and y is 6 and the oligonucleotide is any of at least about 12 or 24 nucleotides in length. In another embodiment, n is 4 and y is 3 and the oligonucleotide is any of at least about 11 or 22 nucleotides in length.

In another embodiment, the c-myc antisense oligonucleotides that prevent translation of an mRNA from a c-myc gene due to RNase-H-mediated degradation of the mRNA from a c-myc gene and/or steric hindrance comprise alternating thiophosphoramidate and thiophosphate linkages. In other embodiments, the oligonucleotide comprises alternating phosphoramidate and thiophosphate linkages. In another embodiment, the oligonucleotide comprises alternating phosphoramidate and phosphate linkages. In another embodiment, the oligonucleotide comprises alternating thiophosphoramidate and phosphate linkages. In another embodiment, the oligonucleotide with alternating thiophosphoramidate and thiophosphate linkages comprises at least about any of 25%-35%, 30%-40%, 35%-45%, 45%-55%, 50%-60%, 55%-65%, or 60-70% thiophosphoramidate linkages. In another embodiment, the oligonucleotide with alternating phosphoramidate and thiophosphate comprises at least about any of 25%-35%, 30%-40%, 35%-45%, 45%-55%, 50%-60%, 55%-65%, or 60-70% phosphoramidate linkages. In another embodiment, the oligonucleotide with alternating thiophosphoramidate and phosphate linkages comprises at least about any of 25%-35%, 30%-40%, 35%-45%, 45%-55%, 50%-60%, 55%-65%, or 60-70% thiophosphoramidate linkages. In another embodiment, the oligonucleotide with alternating phosphoramidate and phosphate comprises at least about any of 25%-35%, 30%-40%, 35%-45%, 45%-55%, 50%-60%, 55%-65%, or 60-70% phosphoramidate linkages. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14) In other embodiments, the oligonucleotide comprises the sequence AACGTTGAGGGGCAT(SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

In some aspects, also provided herein are oligonucleotides comprising a sequence complementary to an mRNA from a c-myc gene, wherein the nucleoside subunits of the oligonucleotide are joined by intersubunit linkages, wherein the oligonucleotide comprises two or more contiguous thiophosphoramidate linkages located on both the 5' and 3' ends of the oligonucleotide, wherein the oligonucleotide is about 6 to about 25 nucleotides in length, and wherein the oligonucleotide is a substrate for RNase-H-mediated degradation of the mRNA from a c-myc gene and/or prevents translation of the mRNA by steric hindrance. In one embodiment, the oligonucleotide is about 6 to about 20 nucleotides or is about 6 to about 30 nucleotides in length. In some embodiments, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length. In one embodiment, the c-myc antisense oligonucleotide is at least about 6 to at least about 50, including at least about 8 to at least about 30, or is about 6 to about 20 nucleotides or is about 6 to about 30 nucleotides or at least about 10 to at least about 20, and at least about 12 to at least about 16 nucleotides in length.

In some embodiments, the c-myc antisense oligonucleotides that prevent translation of an mRNA from a c-myc gene due to RNase-H-mediated degradation of the mRNA from a c-myc gene and/or steric hindrance provided herein comprise at least about 6, 7, 8, 9, 10, 11, 12, 13, 14, 15, 16, 17, 18, 19, 20, 21, 22, 23, 24, or 25 nucleotides in length having a gap of about 2 to 16 nucleotides in length and having 5' and "3' end regions that are independently at least 2 to 16. In other embodiments, exemplary 5' end-gap-3'end configurations for the c-myc antisense gapmer oligonucleotides can be any of the exemplary configurations disclosed above.

In some embodiments, the c-myc antisense oligonucleotide that prevents translation of an mRNA from a c-myc gene due to RNase-H-mediated degradation of the mRNA from a c-myc gene and/or steric hindrance further comprises two or more contiguous thiophosphate or phosphate linkages located in between the two or more contiguous thiophosphoramidate linkages located on both the 5' and 3' ends of the oligonucleotide. In other embodiments, the oligonucleotide comprises five contiguous thiophosphoramidate linkages located on the 5' end of the oligonucleotide, four contiguous thiophosphoramidate linkages located on the 3' end of the oligonucleotide, and six contiguous thiophosphate or phosphate linkages located between the five contiguous thiophosphoramidate linkages located on the 5' end of the oligonucleotide and the four contiguous thiophosphoramidate linkages located on the 3' end of the oligonucleotide. In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14) In other embodiments, the oligonucleotide comprises the sequence AACGTTGAGGGGCAT(SEQ ID NO:1). In another embodiment, the oligonucleotide comprises the sequence UAACGTTGAGGGGCA (SEQ ID NO:2). In one embodiment, when the oligonucleotide comprises UAACGTTGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4).

In other embodiments, the c-myc antisense oligonucleotide that prevents translation of an mRNA from a c-myc gene due to RNase-H-mediated degradation of the mRNA from a c-myc gene and/or steric hindrance is fluorescently labeled. Non-limiting examples of fluorescent labels include fluorescein, phosphor, rhodamine, and polymethine dye derivative. Examples of commercially available fluorescent dyes include BODIPY FL (brand name, manufactured by Molecular Probe Inc.), FluorePrime (trade name, manufactured by Amersham Pharmacia), Fluoredite (trade name, manufactured by Millipore Corporation), FAIL (manufactured by ABI), Cy3 and Cy5 (manufactured by Amersham Pharmacia), and tetramethylrhodamine (TAMRA; manufactured by Molecular Probe Inc.).

Techniques for synthesizing mixed-action oligonucleotides with varying intersubunit linkages can be found, inter alia, in U.S. Pat. No. 7,494,982, the disclosure of which is incorporated herein in its entirety.

In some embodiments, the c-myc antisense oligonucleotide that prevents translation of an mRNA from a c-myc gene due to RNAse H-mediated degradation of the mRNA and/or steric hindrance is an oligonucleotide shown in Table 3.

TABLE 3

Mixed-action antisense oligonucleotides

| ODN # | 5'-d-(Oligonucleotide)-3' | SEQ ID NO: | Type of intersubunit linkage(s) | Mode of action |
|---|---|---|---|---|
| 18 | Palm-TAACGTTGAGGGGCAT | 3 | Alt-NPS/PS | mixed |
| 19 | TAACGTTGAGGGGCAT | 3 | Alt-NPS/PS | mixed |
| 24 | Palm-U-rA-rA-rC-dG-dT-dT-dG-dA-dG-dG-dGdGrCrA | 2 | rNPS/PS/rNPS | mixed |
| 25 | U-rA-rA-rC-dG-dT-dT-dG-dA-dG-dG-dG-dG-rC-rA | 2 | rNPS/PS/rNPS | mixed |
| 34 | Palm-AACGTTGAGGGGCAT-TAMRA | 1 | Alt-NPS/PS | mixed |

*Palm = palmitic acid lipid moiety (see discussion infra);
**TAMRA = fluorescent label;
***underlined and bold nucleotides indicate a different intersubunit linkage;
****alt = alternating;
******r = ribo
All nucleosides are dideoxy unless indicated r = ribo or d = dideoxy.

E. Lipid or Cholesterol Conjugation to Oligonucleotides

In some aspects, any of the c-myc antisense oligonucleotides described herein can be conjugated to a cholesterol or lipid moiety. Conjugation of antisense oligonucleotide have been associated with increased cellular uptake as well as other improved properties for delivering nucleic acids to cells such as, but not limited to, improved pharmacokinetics (see, e.g., U.S. Patent Application Publication No. 2005/0113325, the disclosure of which is incorporated herein by reference).

In some embodiments, any of the c-myc antisense oligonucleotides described herein can be conjugated to a cholesterol moiety to facilitate oligonucleotide delivery into a target cell or tissue (such as, but not limited to, a cancer cell or a tumor). In some embodiments, a cholesterol moiety is a cholesterol molecule, sterol or any compound derived from cholesterol including chlolestanol, ergosterol, stimastanol, stigmasterol, methyl-lithocholic acid, Cortisol, corticosterone, A5-pregnenolone, progesterone, deoxycorticosterone, 17-OH-pregnenolone, 17-OH-progesterone, 11-dioxycortisol, dehydroepiandrosterone, dehydroepiandrosterone sulfate, androstenedione, aldosterone, 18-hydroxycorticosterone, tetrahydrocortisol, tetrahydrocortisone, cortisone, prednisone, 6α-methylpredisone, 9α-fluoro-16a-hydroxyprednisolone, 9α-fluoro-16amethylprednisolone, 9α-fluorocortisol, testosterone, dihydrotestosterone, androstenediol, androstenedione, androstenedione, 3α,5α-androstanediol, estrone, estradiol, estrogen, spermidine cholesterol carbamate, N4-spermidine cholesteryl carbamate, N4-spermidine cholesteryl carbamate di HCl salt, N4-spermidine-7 dehydro cholesteryl carbamate, N4-spermine cholesteryl carbamate, N,N bis(3-aminopropyl) cholesteryl carbamate, N,N bis(6-aminohexyl) cholesteryl carbamate, N4-spermidine dihydrocholesteryl carbamate, N4-spermidine lithocholic carbamate methyl ester, N1,N8-bis(3-aminopropyl-N4-spermidine cholesteryl carbamate, N(N4-3-aminopropylspermidine) cholesteryl carbamate, N,N-bis(4-aminobutyl) cholesteryl carbamate, N4-spermidine cholesteryl urea, N4-spermine cholesteryl urea, N4-spermidine dihydro cholesteryl urea, N4-spermine dihydro cholesteryl urea, N,N-bis(N'-3-aminopropyl-N"4aminobutyl) cholesteryl carbamate, N4-spermidine cholesteryl carboxamide, and N—[N1,N4,N8-tris(3-aminopropyl)spermidine]cholesteryl carbamate, lumisterol, cholic acid, desoxycholic acid, chenodesoxycholic acid and lithocholic acid and derivatives thereof.

In other embodiments, any of the c-myc antisense oligonucleotides described herein can be conjugated to a lipid moiety to facilitate oligonucleotide delivery into a target cell or tissue (such as, but not limited to, a cancer cell or a tumor). The conjugated lipid moiety can be any lipid or lipid derivative that provides enhanced cellular uptake compared to the unmodified oligonucleoside. In some embodiments, the lipids are linear hydrocarbons, saturated or unsaturated, fatty acids, or fatty acid derivatives, such as fatty amides. The length of the hydrocarbon chain can be from $C_8$-$C_{22}$. Examples of saturated hydrocarbons include, but are not limited to, octane ($C_8H_{20}$), nonane ($C_9H_{20}$), decane ($C_{10}H_{22}$), undecane ($C_{11}H_{24}$), dodecane ($C_{12}H_{26}$), and tridecane ($C_{13}H_{28}$). Other nonlimiting examples of saturated hydrocarbons are depicted in Table 4.

TABLE 4

Saturated hydrocarbons

| Systematic name | Carbon chain |
|---|---|
| Tetradecane | $C_{14}H_{30}$ |
| Pentadecane | $C_{15}H_{32}$ |
| Hexadecane | $C_{16}H_{34}$ |
| Heptadecane | $C_{17}H_{36}$ |
| Octadecane | $C_{18}H_{38}$ |
| Nonadecane | $C_{19}H_{40}$ |
| Eicosane | $C_{20}H_{42}$ |

In other embodiments, mono- and poly-unsaturated forms (alkenes and polyenes, such as alkadienes and alkatrienes) of hydrocarbons can also be selected. In some embodiments, mono- and poly-unsaturated lipid moieties having one to three double bonds can be utilized, although moieties having more double bonds can also be employed. In further embodiments, alkynes (containing one or more triple bonds) and alkenynes (containing triple bond(s) and double bond(s)) can also be utilized.

In some embodiments, a fatty alcohol can be selected. In one embodiment, the fatty alcohol is from $C_{16}$ to $C_{20}$, for example, batyl (1-O-Octadecylglycerol ($C_{18}$)).

Other suitable lipid components include simple fatty acids and fatty acid derivatives can be conjugated to any of the c-myc antisense oligonucleotides disclosed herein. In some embodiments, fatty acids and their derivatives can be fully saturated or mono- or poly-unsaturated. The length of the fatty acid or fatty acid derivative chain can be from $C_8$-$C_{22}$.

Examples of saturated fatty acids include, but are not limited to, caprylic acid, capric acid, lauric acid, behenic acid, lignoceric acid, or cerotic acid. Other nonliminiting examples of saturated fatty acids are depicted in Table 5.

TABLE 5

Saturated fatty acids

| Systematic name | Trivial name | Carbon chain |
|---|---|---|
| Tetradecanoic | myristic | 14:0 |
| Hexadecanoic | palmitic | 16:0 |
| Octadecanoic | stearic | 18:0 |
| Eicosanoic | arachidic | 20:0 |

Mono- and poly-unsaturated forms of fatty acids can also be employed. In some embodiments, mono- and poly-unsaturated lipid moieties having one to three double bonds can be employed, although compounds having more double bonds can also be conjugated to the c-myc antisense oligonucleotides. Fatty acids with one or more triple bonds in the carbon chain, as well as branched fatty acids, can also be used in the compounds of the invention. Non-limiting examples of common mono- and poly-unsaturated fatty acids that can be employed include those depicted in Table 6.

TABLE 6

Mono- and poly-unsaturated fatty acids

| Systematic name | Trivial name | Carbon chain |
|---|---|---|
| Cis-9-hexadecanoic | palmitoleic | 16:1 (n-7) |
| Cis-6-octadecanoic | petroselinic | 18:1 (n-12) |
| Cis-9-octadecanoic | oleic | 18:1 (n-9) |
| 9,12-octadecadienoic | linoleic | 18:2 (n-6) |
| 6,9,12-octadecatrienoic | gamma-linolenic | 18:3 (n-6) |
| 9,12,15-octadecatrienoic | alpha-linolenic | 18:3 (n-3) |
| 5,8,11,14-eicosatetraenoic | arachidonic | 20:4 (n-6) |

The linkage between the oligonucleotide and the lipid moiety may be a direct linkage, or it may be via an optional linker moiety. The linker moiety may also serve to facilitate the chemical synthesis of the compounds. Whether or not a linker group is used to mediate the conjugation of the oligonucleotide and the lipid moiety components, there are multiple sites on oligonucleoside components of the oligonucleotide to which the lipid moiety(ies) may be conveniently conjugated. Suitable linkage points include the 5' and 3' termini, one or more sugar rings, the internucleoside backbone and the nucleobases of the oligonucleoside. Typically, the lipid moiety is attached to the 3' or 5' terminus of the oligonucleoside.

If the lipid moiety is to be attached to the 3' terminus, the attachment may be directly to the 3' substituent, such as a 3'-amino group or 3'-hydroxy group. Alternatively, the lipid moiety may be linked via a 3'-linked phosphate group. If the lipid moiety is to be linked to the 5' terminus, it is typically attached through a 5'-linked phosphate group.

Attachment of the lipid moiety to a base on the oligonucleoside may through any suitable atom, for example to the $N^2$ amino group of guanosine.

Examples of preferred linker groups x include amino glycerol and O-alkyl glycerol-type linkers, which can be depicted, respectively, by the generic structures:

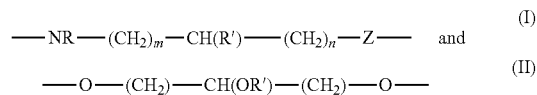

where R is either H or methyl; R'=H, OH, $NH_2$ or SH; Z=O, S or NR; and n and m are independently integers between 1-18. Specific examples of suitable linkers are an aminoglycerol linker, in which R'=OH, Z=O, and m and n are each 1 (formula I); a bis-aminoglycerol linker, in which R'=OH, Z=NH, and m and n are each 1 (formula I); and an O-alkyl glycerol linker, in which R'=H (formula II).

In some embodiments, one or two lipid or cholesterol moieties can be conjugated to a c-myc antisense oligonucleotide. In some embodiments, the one or two lipid or cholesterol moieties can be conjugated to a c-myc antisense oligonucleotide by a linker, such as any of the linkers disclosed above. Where one lipid or cholesterol moiety is used, it can be conjugated to either the 5' or 3' end of the oligonucleotide. When two lipid or cholesterol moieties are conjugated to the oligonucleotide, each lipid or cholesterol moiety component can be identical or can be selected independently. In some embodiments of the present invention, a palmitic acid lipid moiety is not conjugated to a c-myc antisense oligonucleotide wherein the intersubunit linkages of the oligonucleotide are entirely NPS and wherein the oligonucleotide has the sequence AACGTTGAGGGGCAT (SEQ ID NO:1). In some embodiments, contacting any of the oligonucleotides disclosed herein with a proliferating cell decreases relative c-myc protein expression in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a proliferating cell decreases relative c-myc protein expression in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In other embodiments, contacting any of the oligonucleotides disclosed herein with a population of proliferating cells decreases the relative cell growth rate of the population of cells by greater than at least about 35% (such as at least 40%, 45%, 50%, 55%, 60%, 70%, 75%, 80%, 85%, 90%, 95%, or 100%, inclusive, including any percentages in between these values) in comparison to cells that have not been contacted with the oligonucleotide. In other embodiments, contacting any of the oligonucleotides disclosed herein with a population of proliferating cells decreases the relative cell growth rate of the population of cells by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide. In some embodiments, the oligonucleotide is complementary to an mRNA from a c-myc gene at the site of the mRNA's translation initiation region. In other embodiments, the oligonucleotide is at least 80% complementary (such as at least 85%, 90%, 91%, 92%, 93%, 94%, 95%, 96%, 97%, 98%, 99%, or 100% complementary) to an mRNA from a c-myc gene at the site of the mRNA's translation initiation region. In other embodiments of any of the c-myc antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a c-myc gene at a site on the mRNA where two exons are spliced together. In some embodiments of any of the embodiments herein, the oligonucleotide comprises the sequence ACGTTGAGGGGCAT (SEQ ID NO:15). In some embodiments of any of the embodiments herein, the oligonucleotide comprises the sequence TCGTCGCGGGAGGCTG (SEQ ID NO:16). In some embodiments of any of the embodiments herein, the oligonucleotide has the sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), or TTTCATTGTTTTCCA (SEQ ID NO:4), CTCGTCGTTTCCGCAA-CAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14) In other embodiments, the oligonucleotide comprises the sequence AACGTTGAGGGGCAT (SEQ ID NO:1). In another embodiment, the oligonucleotide comprises the sequence UAACGTTGAGGGGCA (SEQ ID NO:2). In one embodiment, when the oligonucleotide comprises UAACGT-TGAGGGGCA (SEQ ID NO:2), the 5'uridine can be 3'-amino-2'-hydroxy-uridine or 3'-oxy-2'-hydroxy-uridine. In a further embodiment, the oligonucleotide comprises the sequence TAACGTTGAGGGGCAT (SEQ ID NO:3). In yet another embodiment, the oligonucleotide comprises the sequence TTTCATTGTTTTCCA (SEQ ID NO:4). In another embodiment, a palmitic acid is conjugated to the 5' end of the oligonucleotide.

Antisense oligonucleotides of the present invention described as being conjugated to a specified hydrocarbon or a specified fatty acid (with the same number of carbon atoms as the specified hydrocarbon) are closely related and differ in structure only in the nature of the bond that joins the moiety to the oligonucleotide, which in turn is a result of the synthesis procedure used to produce the conjugated compound. For example, when compounds are synthesized having the lipid moiety conjugated to the 3'-amino terminus of an oligonucleoside, the use of the aldehyde form of a fatty acid (a fatty aldehyde) as the starting material results in the formation of an amine linkage between the lipid chain and the oligonucleoside, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated lipid group is used broadly herein to include fatty acid derivatives, including fatty amides). Techniques for conjugating lipid or cholesterol moieties to oligonucleotides can be found, inter alia, in U.S. Pat. No. 7,494,982, the disclosure of which is incorporated herein in its entirety.

E. Modified or Substituted Sugar Moieties.

In some aspects, any of the c-myc antisense oligonucleotides disclosed herein can further comprise one or more modified or substituted sugar moieties. In some embodiments, the oligonucleotides comprise one of the following substitutions at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Other oligonucleotides can comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, CI, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification can include 2'-methoxyethoxy (2'-O—$CH_2CH_2OCH_3$, also known as 2'-O-(2-methoxyethyl) or 2'-MOE) i.e., an alkoxyalkoxy group. A further modification can include 2'-dimethylaminooxyethoxy, i.e., a $O(CH_2)_2ON(CH_3)_2$ group, also known as 2'-DMAOE, as described in examples herein, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$, also described in examples herein.

Other sugar modifications can include 2'-methoxy (2'-O—CH3), 2'-aminopropoxy (2'-OCH2CH2CH2NH2), 2'-allyl (2'-CH2-CH=CH2), 2'-O-allyl (2'-O—CH2-5 CH=CH2) and 2'-fluoro (2'-F). The 2'-modification can be in the arabino (up) position or ribo (down) position. A 2'-arabino modification can be 2'-F. Similar modifications can also be made at other positions on the oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. Representative U.S. patents that teach the preparation of such modified sugar structures include, but are not limited to, U.S. Pat. Nos. 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

F. Nucleobase Modifications

Any of the c-myc antisense oligonucleotides disclosed herein can also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, N-alkyl N-derivatives of 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—O^C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-60 pyrimido[4,5-b]indol-2-one), pyridoindole cytidine (H-pyrido[3',2':4,5]pyrrolo[2,3-d]pyrimidin-2-one). Modified nucleobases can also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability and can be included as base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as 5,502,177; 5,525,711; 5,552,540; 5,587,469; 5,594,121; 5,596,091; 5,614,617; 5,645,985; 5,830,653; 5,763,588; 6,005,096; and 5,681,941, each of which is herein incorporated by reference, and U.S. Pat. No. 5,750,692, which is commonly owned with the instant application and also herein incorporated by reference.

III. Pharmaceutical Compositions

In some aspects of the present invention, when employed as pharmaceuticals, the c-myc antisense oligonucleotides disclosed herein can be formulated with a pharmaceutically acceptable excipient or carrier to be formulated into a pharmaceutical composition.

When employed as pharmaceuticals, the c-myc antisense oligonucleotides can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the c-myc antisense oligonucleotides disclosed herein are protected from acid digestion in the stomach by a pharmaceutically acceptable protectant.

This invention also includes pharmaceutical compositions which contain, as the active ingredient, one or more of the antisense oligonucleotides associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The antisense oligonucleotides are effective over a wide dosage range and are generally administered in a therapeutically effective amount. It will be understood, however, that the amount of the antisense oligonucleotides actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient antisense oligonucleotide is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the c-myc antisense oligonucleotide from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

IV. Methods of the Invention

The antisense oligonucleotides (such as in compositions) disclosed herein can be used for the treatment and/or prevention of a cell proliferative disorder. In some embodiments, the individual is diagnosed with or is suspected of having a cell proliferative disorder.

The present invention is directed to methods for inhibiting the symptoms or conditions (disabilities, impairments) associated with a cell proliferative disorder as described in detail below. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from a cell proliferative disorder, but rather, can encompass a result which includes reducing or preventing the symptoms that result from a cell proliferative disorder, reducing or preventing the occurrence of such symptoms (either quantitatively or qualitatively), reducing the severity of such symptoms or physiological effects thereof, and/or enhancing the recovery of the individual after experiencing a cell proliferative disorder symptoms.

Specifically, a composition of the present invention (such as any of the c-myc antisense oligonucleotides disclosed herein), when administered to an individual, can treat or prevent one or more of the symptoms or conditions associated with a cell proliferative disorder and/or reduce or alleviate symptoms of or conditions associated with this disorder. As such, protecting an individual from the effects or symptoms resulting from an a cell proliferative disorder includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

The methods can be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

A. Cell Proliferative Disorders

A "proliferative disorder" is any cellular disorder in which the cells proliferate more rapidly than normal tissue growth. Thus a "proliferating cell" is a cell that is proliferating more rapidly than normal cells. The proliferative disorder includes, but is not limited to, neoplasms. A "neoplasm" is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms. Other proliferative disorders include, but are not limited to neurofibromatosis.

The c-myc antisense oligonucleotides (such as in compositions) provided herein are useful for modulating disease states associated with dysregulation of c-myc expression in cells. The c-myc gene is involved in multiple biological and physiological functions, including, e.g., cell proliferation. In some embodiments, the cell proliferative disorder is associated with increased expression or activity of c-myc or cellular growth, or both. In some embodiments, the cell proliferation is cancer.

The methods described herein are also useful for treating solid tumors (such as advanced solid tumors). In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma and malignant melanoma), ovarian cancer, colorectal cancer, and pancreatic cancer.

In some embodiments, the method is useful for treating one or more of the following: cutaneous T cell lymphoma (CTCL), leukemia, follicular lymphoma, Hodgkin lymphoma, and acute myeloid leukemia.

In some embodiments, the disease is a cancer of any one of the following: basal cell carcinoma, medulloblastoma, glioblastoma, multiple myeloma, chronic myelogenous leukemia (CML), acute myelogenous leukemia, pancreatic cancer, lung cancer (small cell lung cancer and non-small cell lung cancer), esophageal cancer, stomach cancer, billary cancer, prostate cancer, liver cancer, hepatocellular cancer, gastrointestinal cancer, gastric cancer, and ovarian and bladder cancer. In some embodiments, the cancer is selected from the group consisting of pancreas ductal adenocarcinoma, colon adenocarcinoma, and ovary cystadenocarcinoma. In some embodiments, the cancer is pancreas ductal adenocarcinoma. In some embodiments, the cancer is a tumor that is poorly perfused and/or poorly vascularized.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer.

Other examples of cancers that can be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma.), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/− monocytoid B cells) and/or Nodal (e.g., +/−monocytoid B cells)), splenic marginal zone lymphoma (e.g., +/−villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm.

Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepithelioid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/−enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's lymphoma).

In some embodiments the lymphoid neoplasm (e.g., lymphoma) is Hodgkin's disease. For example, the Hodgkin's disease can be lymphocyte predominance, nodular sclerosis, mixed cellularity, lymphocyte depletion, and/or lymphocyte-rich.

In some embodiments, the cancer is leukemia. In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

B. Methods of Treating Cell Proliferative Disorders

Provided herein are methods for inhibiting or decreasing c-myc-mediated cell proliferation, said method comprising administering to an individual in need thereof a therapeutically effective amount of a c-myc antisense oligonucleotide (such as in a composition) described herein. In some embodiments, the cell proliferative disorder is associated with increased expression or activity of c-myc or cellular growth, or both. In some embodiments, the cell proliferation is cancer. In some embodiments, the cancer is liver cancer, lymphoma, lung cancer, glioblastoma, pancreatic cancer, sarcoma, renal cell carcinoma, gastric cancer, colorectal cancer, or breast cancer. In some embodiments, the cancer is stage IIIb and/or stage IV. In some embodiments, the cancer is locally advanced or metastatic cancer. In some embodiments, the cancer is c-myc positive (i.e. the cancer cells express c-myc, for example, as determined by immunohistochemistry (IHC)). In further embodiments of any of the methods described herein, administration of the c-myc antisense oligonucleotide (such as any of the c-myc antisense oligonucleotides disclosed herein) comprises contacting one or more cancer cells with the oligonucleotide. In one embodiment, administration of the therapeutically effective amount of one or more of the oligonucleotides results in one or more of reduced cellular proliferation, increased apoptosis, or cellular senescence. In another embodiment, administration of the therapeutically effective amount of one or more of the oligonucleotides does not result in significant toxicity or morbidity in the individual. In some embodiments, the individual is a human.

Also, provided herein are methods of treating a pathological condition associated with dysregulation of c-myc expression in a subject, said method comprising administering to an individual in need thereof a therapeutically effective amount of a c-myc antisense oligonucleotide (such as in a composition) described herein. In some embodiments, the cell proliferative disorder is associated with increased expression or activity of c-myc or cellular growth, or both. In some embodiments, the cell proliferation is cancer. In some embodiments, the cancer is liver cancer, lymphoma, lung cancer, glioblastoma, pancreatic cancer, sarcoma, renal cell carcinoma, gastric cancer, colorectal cancer, or breast cancer. In some embodiments, the cancer is stage IIIb and/or stage IV. In some embodiments, the cancer is locally advanced or metastatic cancer. In some embodiments, the therapy is second line or third line therapy. In some embodiments, the cancer is c-myc positive (i.e. the cancer cells express c-myc for example, as determined by immunohistochemistry (IHC)). In further embodiments of any of the methods described herein, administration of the c-myc antisense oligonucleotide (such as any of the c-myc antisense oligonucleotides disclosed herein) comprises contacting one or more cancer cells with the oligonucleotide. In one embodiment, administration of the therapeutically effective amount of one or more of the oligonucleotides results in one or more of reduced cellular proliferation, increased apoptosis, or cellular senescence. In another embodiment, administration of the therapeutically effective amount of one or more of the oligonucleotides does not result in significant toxicity or morbidity in the individual. In some embodiments, the individual is a human.

Also provided herein are methods of inhibiting the growth of a cell that expresses c-myc, said method comprising administering to an individual in need thereof a therapeutically effective amount of a c-myc antisense oligonucleotide (such as in a composition) described herein. In some embodiments, the cell has abnormally high cellular growth. In some embodiments, the cell is a cancer cell. In some embodiments, the cancer is liver cancer, lymphoma, lung cancer, glioblastoma, pancreatic cancer, sarcoma, renal cell carcinoma, gastric cancer, colorectal cancer, or breast cancer. In some embodiments, the cancer is stage IIIb and/or stage IV. In some embodiments, the cancer is locally advanced or metastatic cancer. In some embodiments, the therapy is second line or third line therapy. In some embodiments, the cancer is c-myc positive (i.e. the cancer cells express c-myc for example, as determined by immunohistochemistry (IHC)). In further embodiments of any of the methods described herein, administration of the c-myc antisense oligonucleotide (such as any of the c-myc antisense oligonucleotides disclosed herein) comprises contacting one or more cancer cells with the oligonucleotide. In one embodiment, administration of the therapeutically effective amount of one or more of the oligonucleotides results in one or more of reduced cellular proliferation, increased apoptosis, or cellular senescence. In another embodiment, administration of the therapeutically effective amount of one or more of the oligonucleotides does not result in significant toxicity or morbidity in the individual. In some embodiments, the individual is a human.

C. Administration of c-Myc Antisense Oligonucleotides

In some embodiments, the c-myc antisense oligonucleotide (such as any of the c-myc antisense oligonucleotides disclosed herein) is administered in the form of an injection. The injection can comprise the compound in combination with an aqueous injectable excipient or carrier. Non-limiting examples of suitable aqueous injectable excipients or carriers are well known to persons of ordinary skill in the art, and they, and the methods of formulating the formulations, may be found in such standard references as Alfonso A R: Remington's Pharmaceutical Sciences, 17th ed., Mack Publishing Company, Easton Pa., 1985. Suitable aqueous injectable excipients or carriers include water, aqueous saline solution, aqueous dextrose solution, and the like, optionally containing dissolution enhancers such as 10% mannitol or other sugars, 10% glycine, or other amino acids. The composition can be injected subcutaneously, intraperitoneally, or intravenously.

In some embodiments, intravenous administration is used, and it can be continuous intravenous infusion over a period of a few minutes to an hour or more, such as around fifteen minutes. The amount administered can vary widely depending on the type of antisense oligonucleotide, size of a unit dosage, kind of excipients or carriers, and other factors well known to those of ordinary skill in the art. The antisense oligonucleotide can comprise, for example, from about 0.001% to about 10% (w/w), from about 0.01% to about 1%, from about 0.1% to about 0.8%, or any range therein, with the remainder comprising the excipient(s) or carrier(s).

For oral administration, the c-myc antisense oligonucleotide can take the form of, for example, tablets or capsules prepared by conventional means with pharmaceutically acceptable excipients or carriers such as binding agents; fillers; lubricants; disintegrants; or wetting agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, and coloring as appropriate.

In some embodiments, the c-myc antisense oligonucleotide can be administered by inhalation through an aerosol spray or a nebulizer that can include a suitable propellant such as, for example, dichlorodifluoromethane, trichlorofluoromethane, dichlorotetrafluoroethane, carbon dioxide, or a combination thereof. In one non-limiting example, a dosage unit for a pressurized aerosol can be delivered through a metering valve. In another embodiment, capsules and cartridges of gelatin, for example, can be used in an inhaler and can be formulated to contain a powderized mix of the compound with a suitable powder base such as, for example, starch or lactose.

In some embodiments, the amount of c-myc antisense oligonucleotide in the composition (such as a pharmaceutical composition) is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a of c-myc antisense oligonucleotide in the effective amount of the pharmaceutical composition (e.g., a unit dosage form) is in the range of about 5 mg to about 500 mg, such as about 30 mg to about 300 mg or about 50 mg to about 200 mg. In some embodiments, the concentration of the of c-myc antisense oligonucleotide in the pharmaceutical composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the of c-myc antisense oligonucleotide is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a of c-myc antisense oligonucleotide in the pharmaceutical composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$. In various embodiments, the pharmaceutical composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a of c-myc antisense oligonucleotide. In some embodiments, the amount of the of c-myc antisense oligonucleotide per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a of c-myc antisense oligonucleotide in the pharmaceutical composition is included in any of the following ranges: about 1 to about 5 mg/m2, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a of c-myc antisense oligonucleotide in the pharmaceutical composition is about 5 to about 300 mg/m$^2$, such as about 20 to about 300 mg/m$^2$, about 50 to about 250 mg/m$^2$, about 100 to about 150 mg/m$^2$, about 120 mg/m$^2$, about 130 mg/m$^2$, or about 140 mg/m$^2$, or about 260 mg/m2

In some embodiments of any of the above aspects, the effective amount of a c-myc antisense oligonucleotide in the pharmaceutical composition includes at least about any of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various embodiments, the effective amount of a of c-myc antisense oligonucleotide in the pharmaceutical composition includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a of c-myc antisense oligonucleotide.

Exemplary dosing frequencies for the pharmaceutical compositions (such as a pharmaceutical composition containing any of the c-myc antisense oligonucleotides disclosed herein) include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the pharmaceutical composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

D. Combination Therapy

In some aspects, any of the methods disclosed herein can further comprise administering to the individual a therapeutically effective amount (such as any of the therapeutically effective amounts described above) of one or more additional anticancer therapeutic agents in addition to any of the c-myc antisense oligonucleotides disclosed herein (such as in a pharmaceutical composition). Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (Podophyllum peltatum).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes. Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase). Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

V. Kits and Articles of Manufacture

In one embodiment, the invention provides an article of manufacture that includes a pharmaceutical composition containing an inhibitor of the invention for any of the uses and methods of the invention. Such articles may be a useful device such as a sustained release device, bandage, transdermal patch or a similar device. The device holds a therapeutically effective amount of a pharmaceutical composition, such as any of the pharmaceutical compositions described herein. The device may be packaged in a kit along with instructions for using the pharmaceutical composition for any of the uses or methods described herein. The pharmaceutical composition includes at least one c-myc antisense oligonucleotide of the present invention, in a therapeutically effective amount such that the use or method is accomplished.

EXAMPLES

Example 1

Effects of c-Myc Antisense Oligonucleotides on c-Myc Protein Expression and Proliferation of Liver Cancer Cells In Vitro This example demonstrates that c-myc antisense oligonucleotide are effective in reducing c-myc protein expression and cell growth in HepG2 liver cancer cells.

Materials and Methods

TABLE 7

Oligonucleotides

| ODN # | 5'-d-(Oligonucleotide)-3' | SEQ ID NO: | Type of intersubunit linkage | Mode of action |
|---|---|---|---|---|
| 1 | Palm-AACGTTGAGGGGCAT | 1 | All-NP | steric blocker |
| 2 | AACGTTGAGGGGCAT | 1 | All-NP | steric blocker |
| 13 | Palm-AACGTTGAGGGGCAT | 1 | All-NP | steric blocker |
| 15 | TAACGTTGAGGGGCAT | 3 | All-NPS | steric blocker |
| 16 | Palm-AACGTTGAGGGGCAT | 1 | NPS/PS/NPS | RNAse-H |
| 17 | TAACGTTGAGGGGCAT | 3 | NPS/PS/NPS | RNAse-H |
| 18 | Palm-TAACGTTGAGGGGCAT | 3 | Alt-NPS/PS | mixed |
| 19 | TAACGTTGAGGGGCAT | 3 | Alt-NPS/PS | mixed |
| 20 | Palm-AACGTTGAGGGGCAT | 1 | NP/PS/NP | RNAse-H |
| 21 | TAACGTTGAGGGGCAT | 3 | NP/PS/NP | RNAse-H |
| 22 | Palm-ATGCCCCTCAACGTT | 5 | All-NPS | Sense control-steric blocker |
| 23 | Palm-ATGCCCCTCAACGTT | 5 | NPS/PS/NPS | RNAse-H-sense control |
| 24 | Palm-U-rA-rA-rC-dG-dT-dT-dG-dA-dG-dG-dG-dG-rC-rA | 2 | rNPS/PS/rNPS | mixed |
| 25 | U-rA-rA-rC-dG-dT-dT-dG-dA-dG-dG-dG-dG-rC-rA | 2 | rNPS/PS/rNPS | mixed |
| 26 | Palm-U-dG-rC-dC-dC-dC-dT-dC-dA-rA-rC-dG-U-U-rA | 17 | rNPS/PS/rNPS | mixed-sense control |
| 27 | U-dG-rC-dC-dC-dC-dT-dC-dA-rA-rC-dG-U-U-rA | 17 | rNPS/PS/rNPS | mixed-sense control |
| 28 | TAACGTTGAGGGGCAT | 3 | All NP | Steric blocker |
| 29 | TAACGTTGAGGGGCAT-TAMRA | 3 | All-NP | steric blocker |
| 30 | Palm-AACGTTGAGGGGCAT-TAMRA | 1 | All-NP | steric blocker |
| 31 | Palm-AACGTTGAGGGGCAT-TAMRA | 1 | All-NPS | steric blocker |
| 32 | Palm-AACGTTGAGGGGCAT-TAMRA | 1 | NPS/PS/NPS | RNAse-H |
| 33 | TAACGTTGAGGGGCAT-TAMRA | 3 | NPS/PS/NPS | RNAse-H |
| 34 | Palm-AACGTTGAGGGGCAT-TAMRA | 1 | Alt-NPS/PS | mixed |
| 35 | TAACGTTGAGGGGCAT-TAMRA | 3 | NP/PS/NP | RNAse-H |
| 36 | TATGCCCCTCAACGTT | 18 | NPS/PS/NPS | RNAse-H control |
| 37 | TATGCCCCTCAACGTT-TAMRA | 18 | NPS/PS/NPS | RNAse-H control |
| 38 | Palm-TATGCCCCTCAACGTT-TAMRA | 18 | NPS/PS/NPS | RNAse-H control |

*Palm = Palmitic acid lipid moiety (see discussion infra);
**TAMRA = fluorescent label r = ribo; d = dideoxy; all nucleosides are dideoxy unless specified ribo or U.

Cell Culture

For these experiments, approximately 10,000 HepG2 cells were plated in 96 well plates in standard growth media. The cells were treated with AS ODNs 16, 18, 20, 28, 29, 30, 31, 32, 33, 34, 35 and sense control ODNs 23, 36, 37, and 38 for either one, two, three, four or six days at a concentration of either 1 μM or 5 μM.

Assessment of Protein Expression

C-myc protein expression was assessed by Western blot according to standard procedures. Protein levels were normalized to the housekeeping gene Hsp90. Antibodies were obtained from Santa Cruz Biotechnology, Inc. Protein expression was determined by densitometry and normalized to expression in untreated control cells.

Assessment of Relative Cell Growth

Cells were harvested at the times indicated at which time the cells were counted using a hemocytometer. Relative cell growth was then plotted as a percentage normalized to untreated control cells.

Results

Measurements of relative growth rates revealed that HepG2 cells treated with AS ODNs 16, 18, 20 at 1 µM or 5 µM for 6 days grew more slowly in comparison to untreated controls (FIG. 1A). Similarly, relative growth rates indicated that HepG2 cells treated with AS ODNs 16, 18, 20, 28, 30, 31, 32, 33, 34, 35 at 1 µM for 6 and 8 days grew more slowly (less than 50% the growth) in comparison to untreated controls (FIG. 1B).

Figure 2:
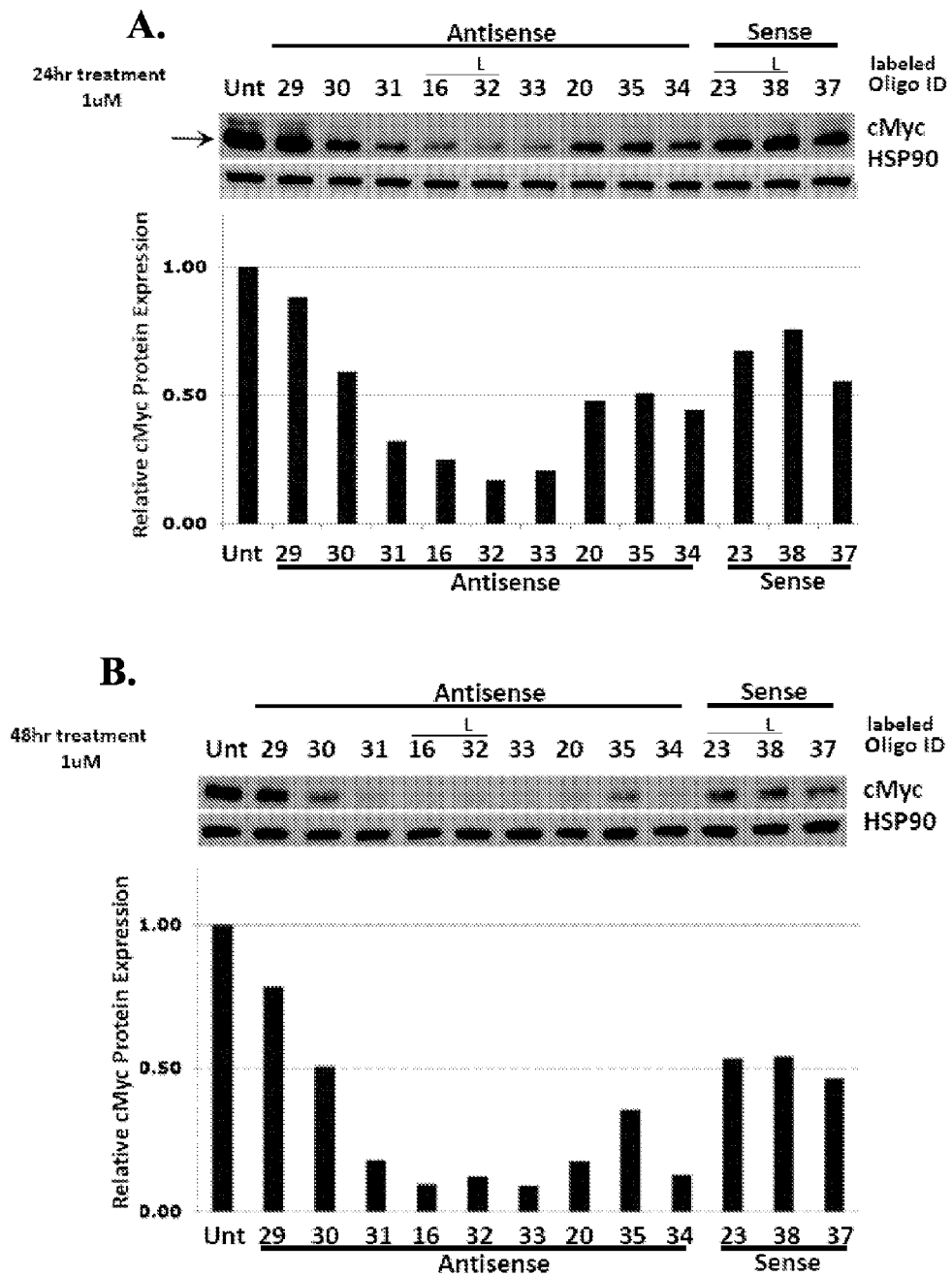
FIG. 2 depicts Western blot analyses of c-myc protein levels in HepG2 cells treated in vitro with antisense c-myc oligonucleotides, sense controls, or untreated controls for one (A), two (B), and three (C) days at 1 µM versus untreated controls. The three day experiment depicted in (C) also utilized the HepG2-Luc cells utilized in the in vivo tumor regression and prevention experiments for determining c-myc protein level following treatment with antisense c-myc oligonucleotides (see Example 3). HSP90 was utilized as a loading control and relative protein expression was normalized versus untreated (Unt) controls. (D). c-myc protein expression in cells treated with AS ODNs 16, 18, 20 at 5 µM for four and five days in comparison to untreated controls.
Figure 2:
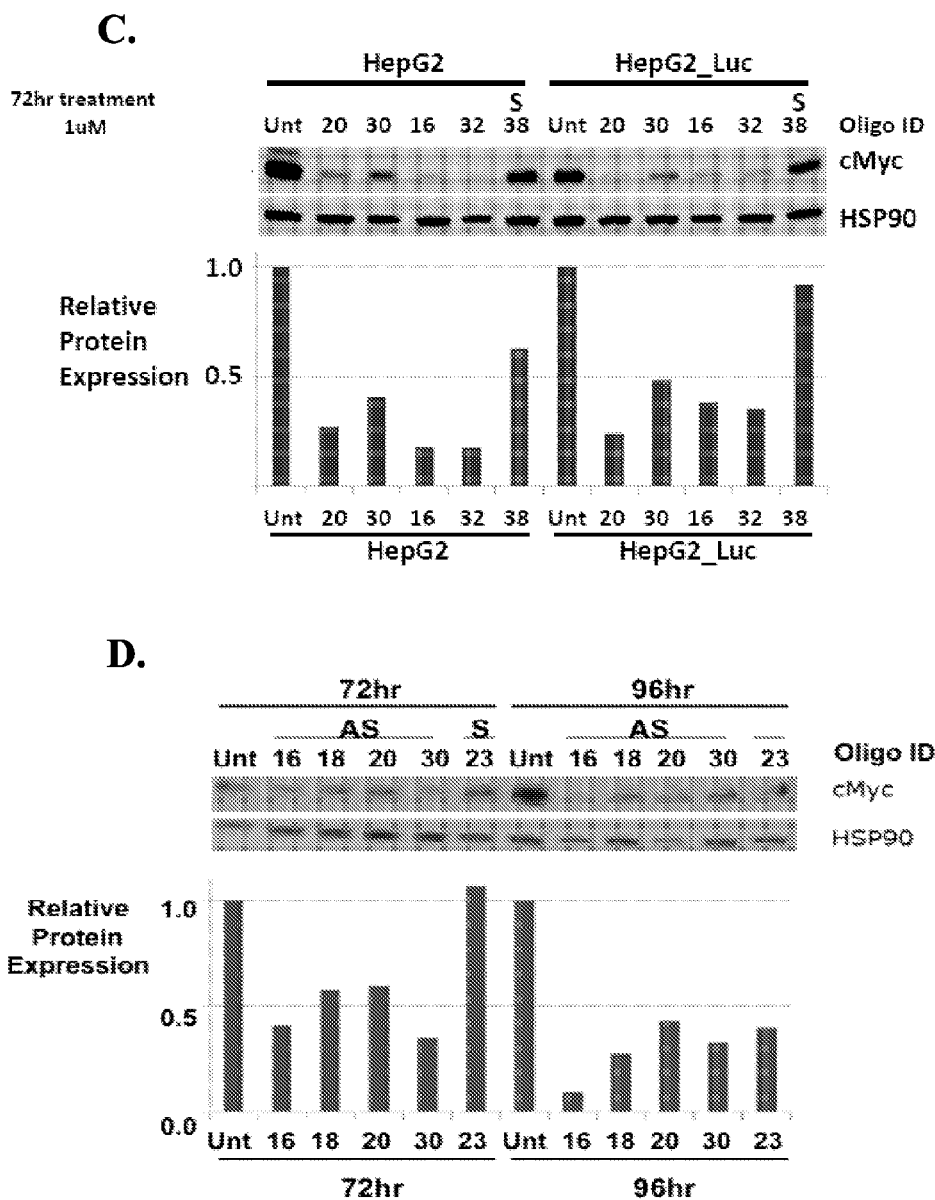

Measurements of relative c-myc protein expression also revealed dramatically decreased expression in HepG2 cells treated with AS ODNs 16, 20, 30, 31, 32, 33, 34, and 35 for one, two, and three days at 1 µM (FIGS. 2A-C), in comparison to untreated controls. Additionally, analysis of relative c-myc protein expression showed decreased expression in cells treated with AS ODNs 16, 18, 20 at 5 µM for four and five days in comparison to untreated controls (FIG. 2D).

This example demonstrated that treatment of a liver cancer cell line in vitro with AS ODNs targeted to c-myc mRNA results in decreased cellular proliferation as well as decreased c-myc protein expression relative to controls.

Example 2

Effects of c-Myc Antisense Oligonucleotides on c-Myc Protein Expression and Proliferation of Follicular Lymphoma Cells In Vitro This example shows that c-myc antisense oligonucleotide are effective in reducing c-myc protein expression and cell growth in VAL follicular lymphoma cancer cells.

Materials and Methods

Cell Culture

For these experiments, approximately 10,000 HepG2 cells were plated in 96 well plates in standard growth media. Cells were treated with AS ODNs 30, 20, 32, 34 and sense control ODN 38 for four days at a concentration of 5 µM.

Assessment of Protein Expression

C-myc protein expression was assessed by Western blot according to standard procedures. Protein levels were normalized to the housekeeping gene Hsp90. Antibodies were obtained from Santa Cruz Biotechnology, Inc. Protein expression was determined by densitometry and normalized to expression in untreated control cells.

Assessment of Relative Cell Growth

Cells were harvested at the times indicated at which time the cells were counted using a hemocytometer. Relative cell growth was then plotted as a percentage normalized to untreated control cells.

Results

Measurements of relative growth rates revealed that the VAL cells treated with AS ODNs 30, 20, 32, 34 at 5 µM grew more slowly in comparison to untreated controls (FIG. 3A). Assays of relative c-myc protein expression also revealed dramatically decreased expression in cells treated with AS ODNs 30, 20, 32, 34 in comparison to untreated controls (FIG. 3B).

This example demonstrated that treatment of a follicular lymphoma cancer cell line in vitro with AS ODNs targeted to c-myc mRNA results in decreased cellular proliferation as well as decreased c-myc protein expression relative to untreated control cells.

Example 3

Effects of c-Myc Antisense Therapy on Cancer Cell Lines In Vivo

This example shows that c-myc antisense ODNs are effective in decreasing tumor volume and weight in both a tumor prevention and regression mouse model.

Materials and Methods

HepG2-Luc liver cancer cells or VAL follicular lymphoma cancer cells (10×106 cells in PBS) were subcutaneously injected into the right flank of 5-6 week old male SCID mice. For the tumor prevention study, HepG2 cells were employed. ODNs were administered by IP injection at a concentration of 30 mg/kg/day three times per week beginning on day 47. Tumor volumes were monitored periodically by calipers. Control animals received injections of PBS.

For the tumor regression analysis, VAL cells were used and after tumor size reached an approximate volume of 5-50 mm3, c-myc antisense ODNs or sense control ODN 23 were administered by IP injection at a concentration of 30 mg/kg/day three times per week beginning on day 13. Control animals received PBS alone for the same period. Antitumor activities of the oligonucleotides were estimated by decreased tumor volume, which was measured with a caliper periodically over the period of the study.

Each point represents mean tumor volume calculated from 4 animals per experimental group. At the end of the study, the animals were sacrificed and the tumors removed and weighed.

Results

In the tumor prevention model using HepG2 liver cancer cells, mice treated with AS ODN 20 exhibited tumors with significantly decreased tumor volumes (p<0.0001) as well as tumor weights (p=0.0021) in comparison to vehicle and sense ODN-treated control (FIGS. 4A and B). As for the tumor regression model using VAL cells, mice treated with AS ODN 16 similarly revealed significantly decreased tumor volumes (p=0.0032) and tumor weights (p=0.0025) compared to vehicle and sense ODN-treated control animals (FIGS. 5C and D).

This example demonstrates that c-myc antisense ODNs can dramatically decrease both tumor volume and weight in both a tumor prevention or regression model using human cancer cells.

Example 4

Effects of c-Myc Antisense Therapy on Primary Murine c-Myc-Induced Cancer In Vivo This example utilizes a conditional mouse model system for producing c-myc-induced hematopoietic tumors to determine the efficacy of c-myc antisense oligonucleotides in treating cancer.

Materials and Methods

Transgenic Mice

The mouse model utilized in these experiments was developed to conditionally overexpress c-myc in the livers of mice when the mice are deprived of the antibiotic doxycyline (see Felsher & Bishop, *Mol. Cell,* 4:199-207, 1999; Shachaf et al., *Nature,* 431:1117, 2004). Transgenic mice were generated using conventional techniques. Founders were derived in FVB/N. Human MYC cDNA exons 2 and 3 were cloned into the EcoR1 site of the polylinker of pUHD10-3 (provided by H. Bujard), which contains the tetracycline response element generating tet-o-MYC. tTA was cloned into the EcoRV site of EμSRα (Felsher & Bishop, *Mol. Cell*, 4:199-207, 1999).

To suppress c-myc transgene expression, mice were administered doxycycline in their drinking water, changed once per week, at a concentration of 100 μg/ml. Upon initiation of the study, doxycycline administration to the mice was halted, resulting in overexpression of c-myc, and primary HCC tumors began to form. Mice were IP administered either c-myc antisense oligonucleotide 20 or 16, sense oligonucleotide 23 at 30 mg/kg/day, three days a week beginning when overall tumor size reached 50 mm³. Control animals received IP injections of PBS.

Histology

Tissues were fixed in 10% buffered formalin, and 5 μm paraffin sections were stained with hematoxylin and eosin (Felsher & Bishop, *Mol. Cell*, 4:199-207, 1999). Sections were also stained following labeling with antibodies to the Ki-67 protein (representative of cellular proliferation) and cleaved caspase 3 (indicating active apoptosis) (Santa Cruz Biotechnology) according to standard techniques. Tissue sections were also stained to detect senescence-associated beta-galactosidase (SA-βgal) activity according to techniques known in the art (see Debacq-Chainiaux et al., *Nature Protocols*, 4(12):1798-1806, 2009).

MRI and Analysis of Tumor Burden

Magnetic Resonance Imaging of tumors was conducted using established techniques. Tumor burden and volume (calculated in cm³) were determined as detailed above.

Results

Figure 6:
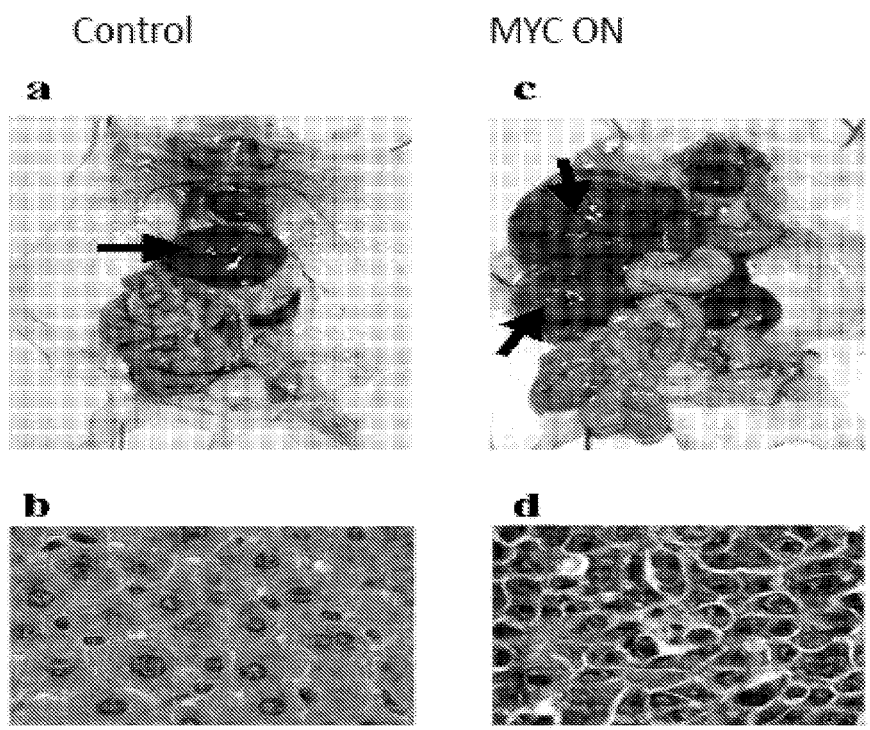
FIG. 6 depicts the effects of overexpressing c-myc in the livers of the transgenic mice used in this study. When mice are deprived of a dietary source of the antibiotic doxycycline, c-myc is overexpressed in hepatic cells resulting in the formation of liver tumors. Gross (A) and H & E-stained tissue (B) histology of livers from control animals. Gross (C) and H & E-stained tissue (D) histology of livers from transgenic animals overexpressing c-myc in hepatocytes.

Hepatocytes in the mice utilized in this experiment have a c-myc gene under control of a tetracycline promoter. Following activation by removing docycyline from the diets of animals, c-myc is overexpressed in the liver resulting in the formation of liver tumors (FIG. 6).

Figure 7:
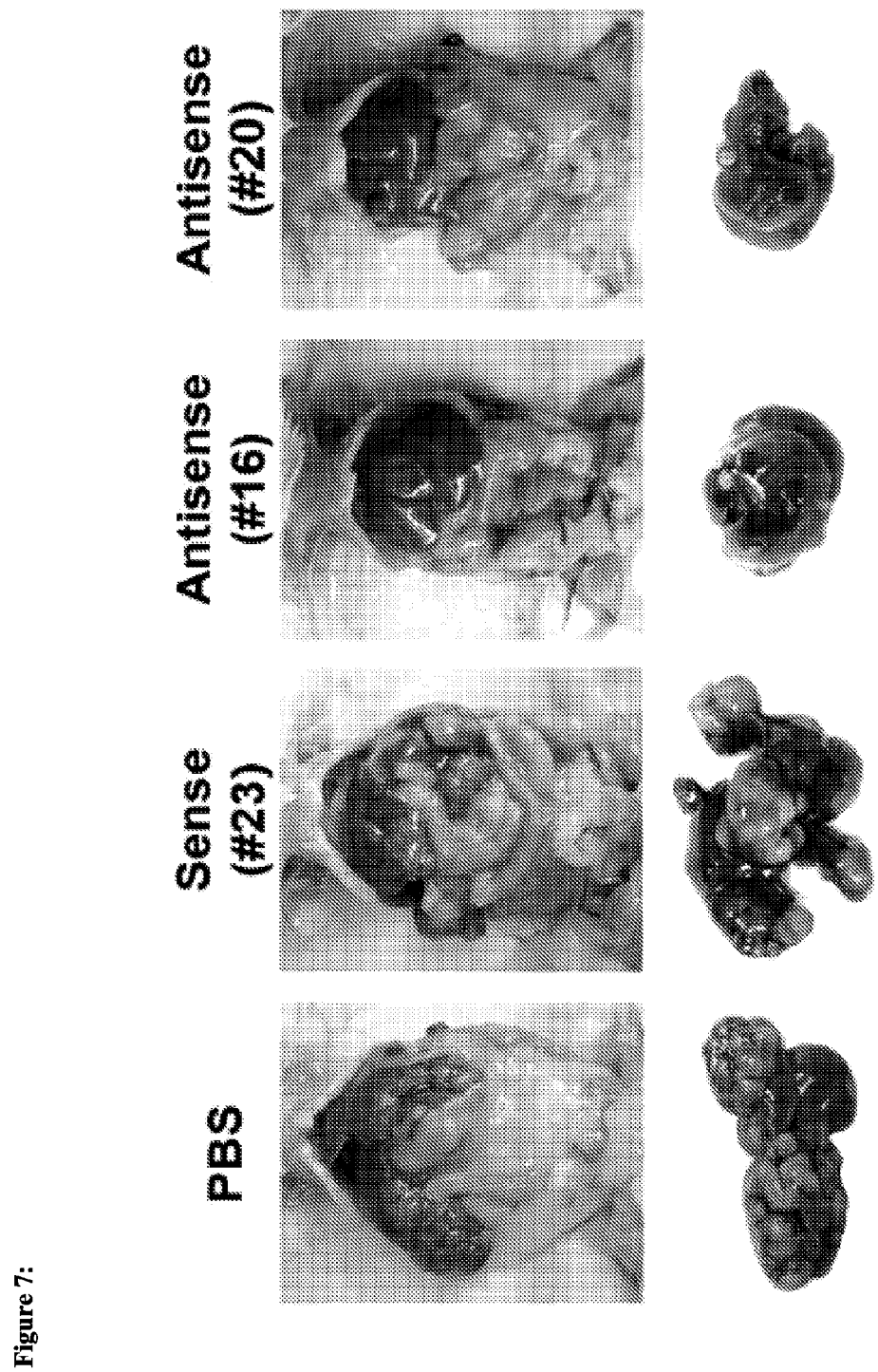
FIG. 7 depicts the gross histological effects of three times weekly 30 mg/kg/day c-myc antisense oligonucleotide treatment on the livers of transgenic mice overexpressing c-myc in hepatocytes versus control transgenic animals treated with vehicle (PBS) or sense oligonucleotide.
Figure 8:
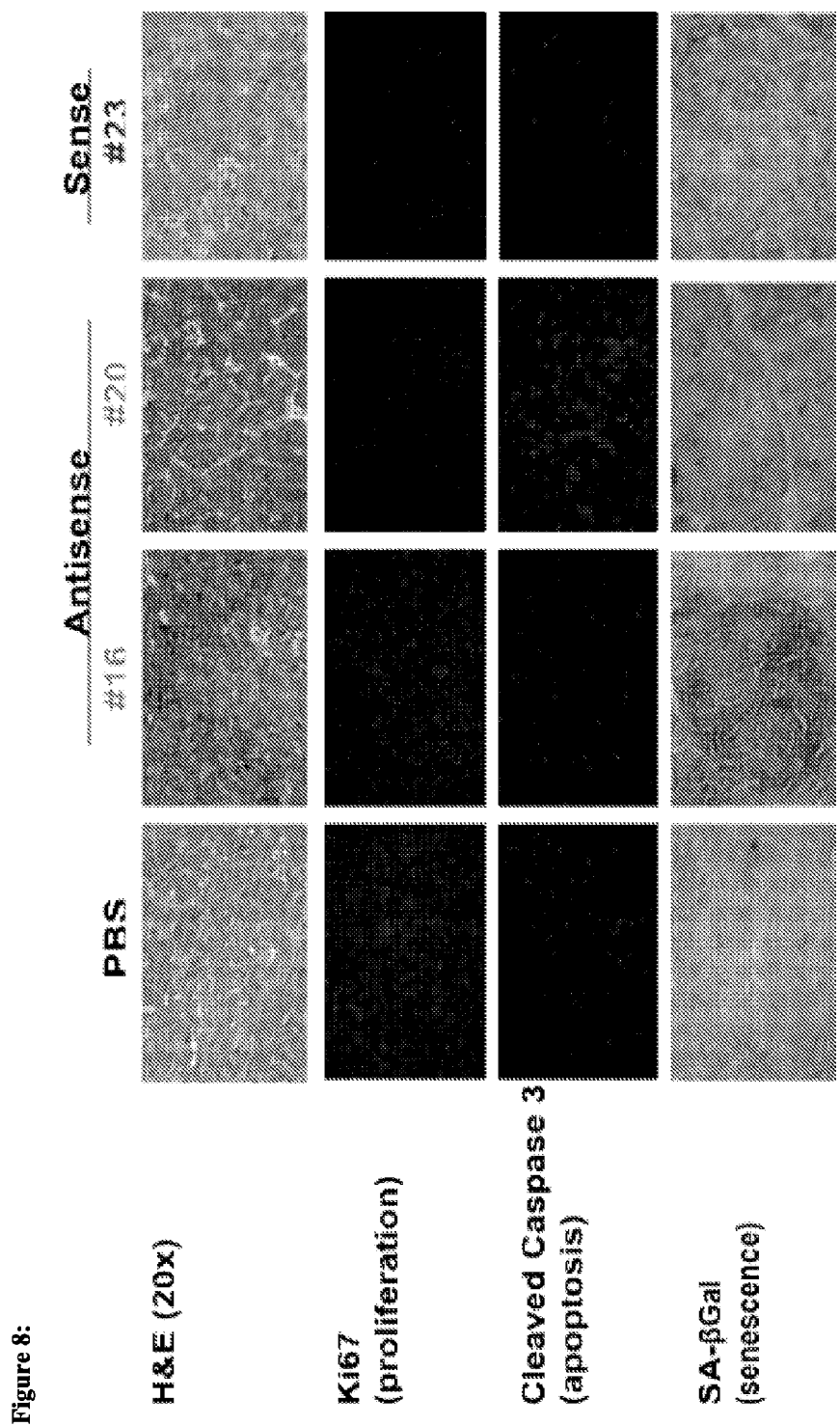
FIG. 8 depicts histological analysis of Ki67 expression, cleaved caspase 3, and SA-βgal in tissue sections of primary tumors from antisense, sense, and vehicle-treated transgenic animals overexpressing c-myc in liver cells.
Figure 9:
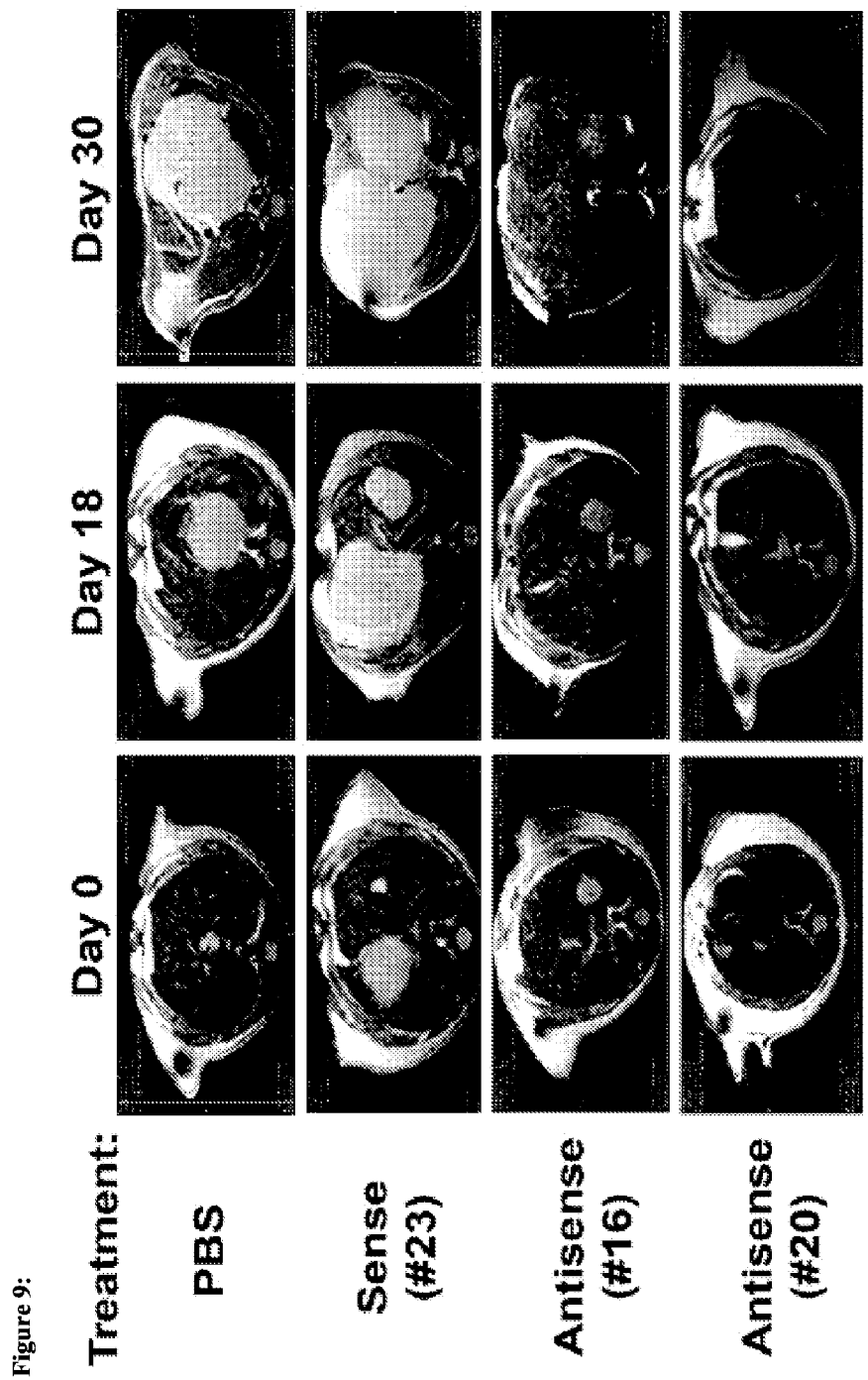
FIG. 9 depicts MRI imaging of tumor growth at days 0, 18, and 30 post initiation of treatment. The images show size and growth of liver tumors in transgenic mice overexpressing c-myc in liver cells that have been treated with antisense c-myc oligonucleotides, sense oligonucleotides, or PBS.

Antisense oligonucleotide treatment with ODNs 16 and 20 of mice actively overexpressing c-myc in their livers dramatically reduced the size of the tumors associated with the livers in comparison with sense oligonucleotide and vehicle-treated controls (FIG. 7). No observable toxicity associated with administration of the antisense ODNs was observed in any of the animals. Histological analysis of primary tumors revealed that tumor cells in mice treated with ODN 20 were actively undergoing apoptosis following staining with an antibody recognizing cleaved caspase 3 (FIG. 8). On the other hand, analysis of primary HCC tumors from animals treated with ODN 16 revealed a high number of cells in senescence based on senescence-associated beta-galactosidase (SA-βgal) activity (FIG. 8). Furthermore, MRI imaging of the mice throughout the study shows that, in contrast to mice treated with vehicle or sense oligonucleotide 23, the liver tumors in mice treated with ODNs 16 or 20 either did not increase in size or actually shrunk as the study progressed (FIG. 9).

Figure 10:
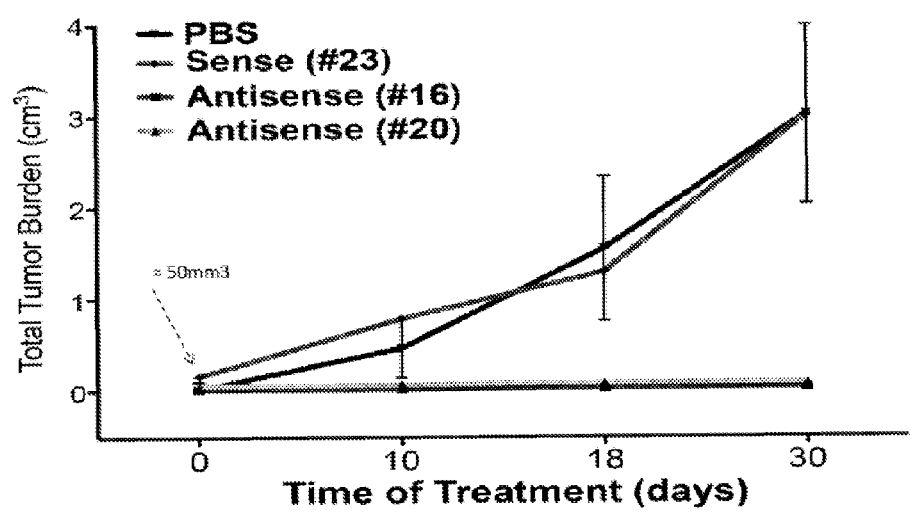
FIG. 10 depicts total tumor burden in the livers of transgenic mice as determined by MRI at days 0, 18, and 30 days post initiation of treatment.
Figure 11:
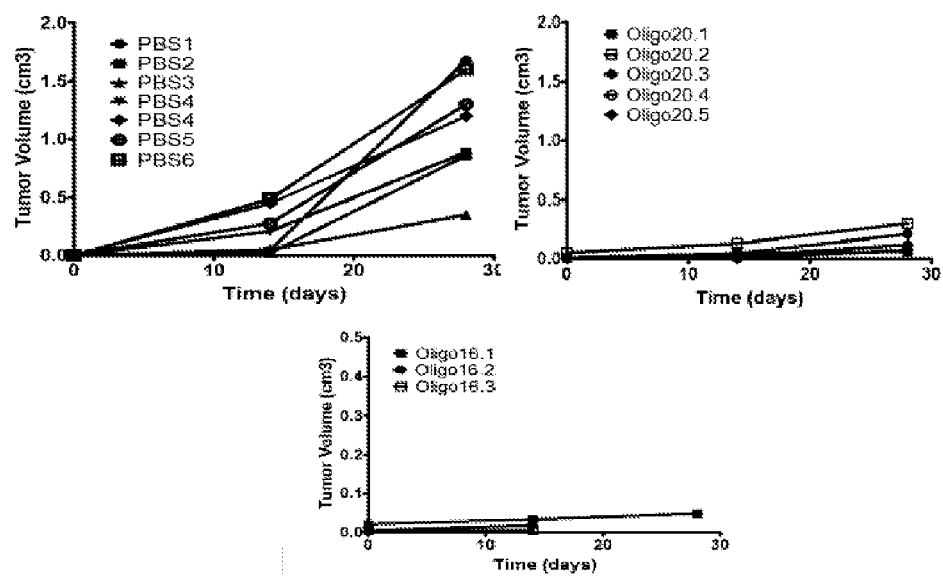
FIG. 11 depicts tumor volume for individual animals in the study treated with PBS (A), c-myc antisense oligonucleotide 20 (B), or c-myc antisense oligonucleotide 16.

Quantitative analysis of the total tumor burden in the study animals again showed that total tumor burden for mice treated with antisense ODNs 16 and 20 remained flat while tumor burden for vehicle and sense ODN-treated animals increased steadily throughout the study (FIGS. 10 and 11).

In summary, antisense oligonucleotides targeted to c-myc have significant activity in primary transgenic mouse models of c-myc-mediated liver cancer. Treatment with the anti-c-myc oligonucleotides is associated with reduced proliferation, increased apoptosis, and increased cellular senescence. Importantly, administration of these oligonucleotides do not result any observed significant toxicity or morbidity in mice treated with them.

Example 5

Effects of c-Myc Antisense Oligonucleotides on c-Myc Protein Expression and Proliferation of Liver Cancer Cells In Vitro Cell Treatment HepG2 cells (obtained from ATCC) were thawed and cultured for 5-25 passages in Eagle's minimal essential medium (EMEM, Invitrogen) plus 10% foetal calf serum (FCS, Hyclone). Cells were treated with antisense PS-oligonucleotides or non-silencing control oligonucleotide (NC) as shown in Table 7 by transfection using Lipofectamine™ RNAiMAX (Invitrogen, Cat#13778) following the manufacturer's protocol. Treated cells were incubated in culture medium for 16-18 hours at 37° C., 5% $CO_2$ prior to fixation or cell lysis for measurement of c-myc protein.

TABLE 8

Oligonucleotides

| Oligo-nucleotide Number | Sequence | SEQ ID NO: | Type of intersubunit linkage |
|---|---|---|---|
| PS4 | CTCGTCGTTTCCGCAACAAG | 6 | All-PS |
| PS7 | ACGTTGAGGGGCATCGTCGC | 7 | All-PS |
| PS16 | AACGTTGAGGGGCATCGTCG | 8 | All-PS |
| PS18 | CTGCTGTCGTTGAGAGGGTA | 9 | All-PS |
| PS23 | GGCATCGTCGCGGGAGGCTGCTGGAGCG | 10 | All-PS |
| PS23.1 | GGCATCGTCGCGGGAGGCTG | 11 | All-PS |
| PS23.2 | TCGTCGCGGGAGGCTGCTGG | 12 | All-PS |
| PS24 | CCGCCCGCTCGCTCCCTCTG | 13 | All-PS |
| PS28 | GTTCTCCTCCTCGTCGCAGT | 14 | All-PS |

Measurement of c-Myc Protein Immunofluroescence

Cells were fixed in 1% formaldehyde for 15 minutes. Cells were then incubated with a rabbit anti-c-myc antibody (cln D84C12, CST) at 5 μg/mL, in block (10% FCS in PBS, 0.1% Triton X-100) at 37° C. for 30', followed by incubation with a fluorescent anti-rabbit-Alexa594 (Invitrogen A21207) antibody at 10 μg/mL in block at 37° C. for 30 minutes. For this second incubation Hoechst was also added to stain cell nuclei. Cells were imaged on a Cellomics Arrayscan HCS imager (Thermoscientific). Five to 10 images per well for a 96-well plate format were taken. HepG2 nuclei were identified by Cellomics software using Hoechst staining. c-myc fluorescence intensity within the same area was measured. The results are shown in FIG. 13.

Western Blotting

Figure 12:
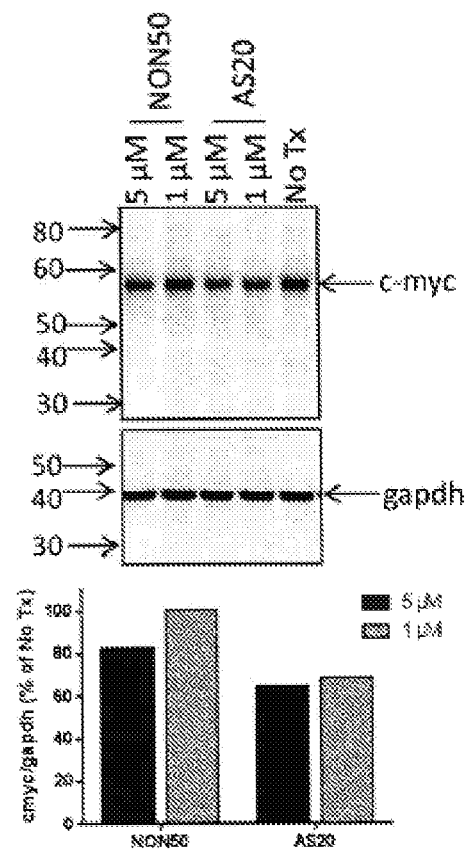
FIG. 12 depicts Western blot analyses of c-myc protein levels in HepG2 cells treated in vitro with antisense c-myc oligonucleotide AS20 (Palm-AACGTTGAGGGGCAT) (NP/PS/NP) (SEQ ID NO:1) and a non-silencing control nucleotide (NON50) from Example 5.

For western blotting, cells were lysed in cell extraction buffer (Invitrogen FNN0011) plus protease (Roche #11836170001) and phosphatase (Pierce #1861277) inhibitors. The BCA assay (Pierce #23227) was used for protein quantitation according to the manufacturer's protocol, and protein concentrations between samples were normalized by dilution when necessary. Samples were heated with Laemmli buffer and proteins were separated electrophoretically on 4-12% Novex Bis-Tris gels (Invitrogen). Proteins were blotted onto a nitrocellulose membrane using wet-electophoretic transfer. Membranes were blocked with 1% milk in Tris-buffered saline (TBS) plus 0.1% Tween detergent. Immunodetection was performed by incubation of the membrane with 10 μg/mL anti-cmyc antibody followed by 0.4 μg/mL anti-rabbit-HRP secondary antibody. C-myc protein was visualized by with ECL2 (Thermofisher) reagent which acts as a substrate for HRP producing a luminescent product via a fluorescent intermediate. Blots were imaged on the Storm imager (GE Healthcare). Band densitometry was performed with imageQuant TL software and blots were reprobed with an anti-GAPDH (a housekeeping protein) antibody to normalize for protein loading. The results are shown in FIG. 12. The antisense oligonucleotides inhibited expression of c-myc protein in a dose dependent manner.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An oligonucleotide comprising a sequence complementary to an mRNA from a c-myc gene, wherein the nucleoside subunits of the oligonucleotide are joined by intersubunit linkages, wherein the oligonucleotide comprises two or more N3'→P5' thiophosphoramidate linkages independently located on both the 5' and 3' ends of the oligonucleotide, wherein the oligonucleotide further comprises two or more contiguous thiophosphate or phosphate linkages located in between the two or more N3'→P5' thiophosphoramidate linkages, wherein the oligonucleotide is about 6 to about 30 nucleotides in length, and wherein the oligonucleotide is a substrate for RNase-H-mediated degradation of the mRNA from a c-myc gene.

2. The oligonucleotide of claim 1, wherein the oligonucleotide comprises five contiguous N3'→P5' thiophosphoramidate linkages located on the 5' end of the oligonucleotide, four contiguous N3'→P5' thiophosphoramidate linkages located on the 3' end of the oligonucleotide, and six contiguous thiophosphate or phosphate linkages located between the five contiguous N3'→P5' thiophosphoramidate linkages located on the 5' end of the oligonucleotide and the four contiguous N3'→P5' thiophosphoramidate linkages located on the 3' end of the oligonucleotide.

3. The oligonucleotide of claim 1, wherein the oligonucleotide is at least 95% complementary to an mRNA from a c-myc gene at the site of the mRNA's translation initiation region.

4. The oligonucleotide of claim 1, wherein the oligonucleotide comprises the sequence ACGTTGAGGGGCAT (SEQ ID NO:15) or the sequence TCGTCGCGGGAGGCTG (SEQ ID NO:16).

5. The oligonucleotide of claim 1 wherein the oligonucleotide comprises a sequence selected from the group consisting of AACGTTGAGGGGCAT (SEQ ID NO:1), UAACGTTGAGGGGCA (SEQ ID NO:2), TAACGTTGAGGGGCAT (SEQ ID NO:3), TTTCATTGTTTTCCA (SEQ ID NO:4), CTCGTCGTTTCCGCAACAAG (SEQ ID NO:6), ACGTTGAGGGGCATCGTCGC (SEQ ID NO:7), AACGTTGAGGGGCATCGTCG (SEQ ID NO:8), CTGCTGTCGTTGAGAGGGTA (SEQ ID NO:9), GGCATCGTCGCGGGAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGCCCGCTCGCTCCCTCTG (SEQ ID NO:13), and GTTCTCCTCCTCGTCGCAGT (SEQ ID NO:14).

6. An oligonucleotide comprising a sequence complementary to an mRNA from a c-myc gene, wherein the nucleoside subunits of the oligonucleotide are joined by intersubunit linkages, wherein the oligonucleotide is a substrate for RNase-H-mediated degradation of the mRNA from a c-myc gene, and
   a. wherein the oligonucleotide comprises at least two contiguous N3'→ P5' thiophosphoramidate intersubunit linkages located on the 5' end of the oligonucleotide;
   b. wherein the oligonucleotide comprises at least two contiguous N3'→ P5' thiophosphoramidate intersubunit linkages located on the 3' end of the oligonucleotide;
   c. wherein the oligonucleotide comprises 2-11 contiguous thiophosphate or phosphate linkages located in between said at least two contiguous N3'→ P5' thiophosphoramidate linkages located on the 5' end and said at least two contiguous N3'→ P5' thiophosphoramidate linkages located on the 3' end of the oligonucleotide; and
   d. wherein the oligonucleotide comprises the sequence AACGTTGAGGGGCAT (SEQ ID NO:1).

7. The oligonucleotide of claim 1, wherein contacting the oligonucleotide with a proliferating cell decreases relative c-myc protein expression in the cell by at least about 50% in comparison to cells that have not been contacted with the oligonucleotide.

8. The oligonucleotide of claim 1, wherein contacting the oligonucleotide with a population of proliferating cells decreases the relative cell growth rate of the population of cells by greater than 50% in comparison to cells that have not been contacted with the oligonucleotide.

9. The oligonucleotide of claim 1, wherein the oligonucleotide further comprises one or more lipid or cholesterol moieties.

10. The oligonucleotide of claim 9, wherein the one or more lipid or cholesterol moieties is/are located on the 5' end of the oligonucleotide, the 3' end of the oligonucleotide, or both the 5' and 3' ends of the oligonucleotide.

11. The oligonucleotide of claim 10, wherein the lipid or the cholesterol moiety is located on the 5' end of the oligonucleotide.

12. The oligonucleotide of claim 10, wherein the lipid moiety comprises a Caprylic acid, a Capric acid, a Lauric acid, a Myristic acid, a Palmitic acid, a Stearic acid, a Arachidic acid, a Behenic acid, a Lignoceric acid, or a Cerotic acid.

13. The oligonucleotide of claim 12, wherein the lipid moiety comprises a Palmitic acid.

14. The oligonucleotide of claim 1 wherein the oligonucleotide further comprises a fluorescent dye label.

15. The oligonucleotide of claim 14, wherein the fluorescent dye label is carboxytetramethylrhodamine (TAMRA).

16. A pharmaceutical composition comprising one or more oligonucleotides of claim 1.

17. The pharmaceutical composition of claim 16, further comprising a pharmaceutically acceptable carrier.

18. A method for treating or preventing a cell proliferative disorder in an individual in need thereof comprising: administering to the individual a therapeutically effective amount of one or more of the oligonucleotides of claim 1 wherein administration of one or more of the oligonucleotides relieves at least one symptom of the cell proliferative disorder.

19. The method of claim 18, wherein the cell proliferative disorder is cancer.

20. The method of claim 19, wherein the cancer is liver cancer or a cancer resulting from B-cell proliferation.

21. The method of claim 18, wherein the individual is human.

22. A kit comprising one or more of the oligonucleotides of claim 1.

23. The oligonucleotide of claim 1, wherein the oligonucleotide comprises two or more contiguous N3'→ P5' thiophosphoramidate linkages independently located on both the 5' and 3' ends of the oligonucleotide.

24. An oligonucleotide comprising a sequence complementary to an mRNA from a c-myc gene, wherein the nucleoside subunits of the oligonucleotide are joined by intersubunit linkages, wherein the oligonucleotide comprises two or more N3'→ P5' thiophosphoramidate or N3'→ P5' phosphoramidate linkages independently located on both the 5' and 3' ends of the oligonucleotide, wherein the oligonucleotide comprises two or more contiguous thiophosphate or phosphate linkages located in between the two or more N3'→ P5' thiophosphoramidate or N3'→ P5' phosphoramidate linkages, wherein the oligonucleotide is about 6 to about 30 nucleotides in length, wherein the oligonucleotide is a substrate for RNase-H-mediated degradation of the mRNA from a c-myc gene, and wherein the oligonucleotide comprises a sequence selected from the group consisting of CTGCTGTCGT-TGAGAGGGTA (SEQ ID NO:9), GGCATCGTCGCGG-GAGGCTGCTGGAGCG (SEQ ID NO:10), GGCATCGTCGCGGGAGGCTG (SEQ ID NO:11), TCGTCGCGGGAGGCTGCTGG (SEQ ID NO:12), CCGC-CCGCTCGCTCCCTCTG (SEQ ID NO:13), GTTCTCCTC-CTCGTCGCAGT (SEQ ID NO:14), and TCGTCGCGG-GAGGCT (SEQ ID NO:16).

25. The oligonucleotide of claim 24, wherein the oligonucleotide comprises two or more contiguous N3'→ P5' thiophosphoramidate or N3'→ P5' phosphoramidate linkages independently located on both the 5' and 3' ends of the oligonucleotide.

26. The oligonucleotide of claim 24, wherein the oligonucleotide comprises five contiguous N3'→ P5' thiophosphoramidate or N3'→ P5' phosphoramidate linkages located on the 5' end of the oligonucleotide, four contiguous N3'→ P5' thiophosphoramidate or N3'→ P5' phosphoramidate linkages located on the 3' end of the oligonucleotide, and six contiguous thiophosphate or phosphate linkages located between the five contiguous N3'→ P5' thiophosphoramidate or N3'→ P5' phosphoramidate linkages located on the 5' end of the oligonucleotide and the four contiguous N3'→ P5' thiophosphoramidate or N3'→ P5' phosphoramidate linkages located on the 3' end of the oligonucleotide.

27. The oligonucleotide of claim 24, wherein contacting the oligonucleotide with a proliferating cell decreases relative c-myc protein expression in the cell by at least about 50% in comparison to cells that have not been contacted with the oligonucleotide.

28. The oligonucleotide of claim 24, wherein contacting the oligonucleotide with a population of proliferating cells decreases the relative cell growth rate of the population of cells by greater than 50% in comparison to cells that have not been contacted with the oligonucleotide.

29. The oligonucleotide of claim 24, wherein the oligonucleotide further comprises one or more lipid or cholesterol moieties.

30. The oligonucleotide of claim 29, wherein the one or more lipid or cholesterol moieties is/are located on the 5' end of the oligonucleotide, the 3' end of the oligonucleotide, or both the 5' and 3' ends of the oligonucleotide.

31. The oligonucleotide of claim 30, wherein the lipid or the cholesterol moiety is located on the 5' end of the oligonucleotide.

32. The oligonucleotide of claim 30, wherein the lipid moiety comprises a Caprylic acid, a Capric acid, a Lauric acid, a Myristic acid, a Palmitic acid, a Stearic acid, a Arachidic acid, a Behenic acid, a Lignoceric acid, or a Cerotic acid.

33. The oligonucleotide of claim 32, wherein the lipid moiety comprises a Palmitic acid.

34. The oligonucleotide of claim 24, wherein the oligonucleotide further comprises a fluorescent dye label.

35. The oligonucleotide of claim 34, wherein the fluorescent dye label is carboxytetramethylrhodamine (TAMRA).

36. A pharmaceutical composition comprising one or more oligonucleotides of claim 24.

37. The pharmaceutical composition of claim 36, further comprising a pharmaceutically acceptable carrier.

38. A kit comprising one or more of the oligonucleotides of claim 24.

39. The oligonucleotide of claim 1 wherein the oligonucleotide is selected from the group consisting of ODN No. 16 (corresponding to the nucleic acid sequence of SEQ ID NO: 1), ODN No. 17 (corresponding to the nucleic acid sequence of SEQ ID NO: 3), ODN No. 32 (corresponding to the nucleic acid sequence of SEQ ID NO: 1), and ODN No.33 (corresponding to the nucleic acid sequence of SEQ ID NO: 3), as shown in Table 7.

* * * * *

SEQUENCE LISTING

```
<160> NUMBER OF SEQ ID NOS: 18

<210> SEQ ID NO 1
<211> LENGTH: 15
<212> TYPE: DNA
<213> ORGANISM: Homo sapiens

<400> SEQUENCE: 1
aacgttgagg ggcat                                                  15

<210> SEQ ID NO 2
<211> LENGTH: 15
<212> TYPE: DNA
<213> ORGANISM: Homo sapiens

<400> SEQUENCE: 2
uaacgttgag gggca                                                  15

<210> SEQ ID NO 3
<211> LENGTH: 16
<212> TYPE: DNA
<213> ORGANISM: Homo sapiens

<400> SEQUENCE: 3
taacgttgag gggcat                                                 16

<210> SEQ ID NO 4
<211> LENGTH: 15
<212> TYPE: DNA
<213> ORGANISM: Homo sapiens

<400> SEQUENCE: 4
tttcattgtt ttcca                                                  15

<210> SEQ ID NO 5
<211> LENGTH: 15
<212> TYPE: DNA
<213> ORGANISM: Homo sapiens

<400> SEQUENCE: 5 atgccctca acgtt                                                   15

<210> SEQ ID NO 6
<211> LENGTH: 20
```

```
<212> TYPE: DNA
<213> ORGANISM: Homo sapiens

<400> SEQUENCE: 6
ctcgtcgttt ccgcaacaag                                              20

<210> SEQ ID NO 7
<211> LENGTH: 20
<212> TYPE: DNA
<213> ORGANISM: Homo sapiens

<400> SEQUENCE: 7
acgttgaggg gcatcgtcgc                                              20

<210> SEQ ID NO 8
<211> LENGTH: 20
<212> TYPE: DNA
<213> ORGANISM: Homo sapiens

<400> SEQUENCE: 8
aacgttgagg ggcatcgtcg                                              20

<210> SEQ ID NO 9
<211> LENGTH: 20
<212> TYPE: DNA
<213> ORGANISM: Homo sapiens

<400> SEQUENCE: 9
ctgctgtcgt tgagagggta                                              20

<210> SEQ ID NO 10
<211> LENGTH: 28
<212> TYPE: DNA
<213> ORGANISM: Homo sapiens

<400> SEQUENCE: 10
ggcatcgtcg cgggaggctg ctggagcg                                     28

<210> SEQ ID NO 11
<211> LENGTH: 20
<212> TYPE: DNA
<213> ORGANISM: Homo sapiens

<400> SEQUENCE: 11
ggcatcgtcg cgggaggctg                                              20

<210> SEQ ID NO 12
<211> LENGTH: 20
<212> TYPE: DNA
<213> ORGANISM: Homo sapiens

<400> SEQUENCE: 12
tcgtcgcggg aggctgctgg                                              20

<210> SEQ ID NO 13
<211> LENGTH: 20
<212> TYPE: DNA
<213> ORGANISM: Homo sapiens

<400> SEQUENCE: 13
ccgcccgctc gctccctctg                                              20

<210> SEQ ID NO 14
```

```
<211> LENGTH: 20
<212> TYPE: DNA
<213> ORGANISM: Homo sapiens

<400> SEQUENCE: 14
gttctcctcc tcgtcgcagt                                              20

<210> SEQ ID NO 15
<211> LENGTH: 14
<212> TYPE: DNA
<213> ORGANISM: Homo sapiens

<400> SEQUENCE: 15
acgttgaggg gcat                                                    14

<210> SEQ ID NO 16
<211> LENGTH: 16
<212> TYPE: DNA
<213> ORGANISM: Homo sapiens

<400> SEQUENCE: 16
tcgtcgcggg aggctg                                                  16

<210> SEQ ID NO 17
<211> LENGTH: 15
<212> TYPE: DNA
<213> ORGANISM: Artificial sequence
<220> FEATURE:
<223> OTHER INFORMATION: mixed sense control

<400> SEQUENCE: 17
ugcccctcaa cguua                                                   15

<210> SEQ ID NO 18
<211> LENGTH: 16
<212> TYPE: DNA
<213> ORGANISM: Artificial sequence
<220> FEATURE:
<223> OTHER INFORMATION: RNAse-H control

<400> SEQUENCE: 18
tatgcccctc aacgtt                                                  16
```